(12) United States Patent
Park et al.

(10) Patent No.: US 12,564,202 B2
(45) Date of Patent: Mar. 3, 2026

(54) COMPOSITION FOR ALLEVIATING, PREVENTING OR TREATING SARCOPENIA, CONTAINING WHEY PROTEIN HYDROLYSATE AS ACTIVE INGREDIENT

(71) Applicant: Neo Cremar Co., Ltd., Seoul (KR)

(72) Inventors: Hyoung Su Park, Pyeongtaek-si (KR); Jae Hwan Kim, Seoul (KR); Joong-chul Shin, Seoul (KR); Seung-Il Ahn, Seoul (KR); Se Young Jung, Seoul (KR); Seok Jun Park, Pyeongtaek-si (KR); Jung Sik Park, Pyeongtaek-si (KR)

(73) Assignee: Neo Cremar Co., Ltd., Seoul (KR)

( * ) Notice: Subject to any disclaimer, the term of this patent is extended or adjusted under 35 U.S.C. 154(b) by 753 days.

(21) Appl. No.: 17/763,726

(22) PCT Filed: Sep. 25, 2020

(86) PCT No.: PCT/KR2020/013116
§ 371 (c)(1),
(2) Date: Mar. 25, 2022

(87) PCT Pub. No.: WO2021/060927
PCT Pub. Date: Apr. 1, 2021

(65) Prior Publication Data
US 2022/0322700 A1 Oct. 13, 2022

(30) Foreign Application Priority Data

Sep. 25, 2019 (KR) ......................... 10-2019-0118146
Sep. 24, 2020 (KR) ......................... 10-2020-0124083

(51) Int. Cl.
| | |
|---|---|
| *A23L 33/18* | (2016.01) |
| *A23C 21/02* | (2025.01) |
| *A23J 3/34* | (2006.01) |
| *A61K 38/01* | (2006.01) |
| *A61P 21/00* | (2006.01) |

(52) U.S. Cl.
CPC .............. *A23J 3/347* (2013.01); *A23L 33/18* (2016.08); *A61K 38/01* (2013.01); *A61P 21/00* (2018.01)

(58) Field of Classification Search
CPC ......... A23L 33/18; A61K 38/01; A23C 21/02; A61P 21/00
See application file for complete search history.

(56) References Cited

U.S. PATENT DOCUMENTS

2008/0254505 A1 * 10/2008 Budolfsen ............... A23J 3/343
435/68.1

FOREIGN PATENT DOCUMENTS

| | | | | |
|---|---|---|---|---|
| JP | 2001333794 A | * 12/2001 | ............. | A23L 1/305 |
| JP | 20100150160 A | 7/2010 | | |
| JP | 2014-193821 A | 10/2014 | | |
| JP | 2016-220628 A | 12/2016 | | |
| JP | 2019-131494 A | 8/2019 | | |
| KR | 10-2008-0082041 A | 9/2008 | | |
| KR | 100866974 B1 | * 11/2008 | ............. | A23L 33/19 |
| KR | 10-2009-0005202 A | 1/2009 | | |
| WO | WO 2017/026429 A1 | 2/2017 | | |

OTHER PUBLICATIONS

Dryakova et al. Antioxidant properties of whey protein hydrolysates as measured by three methods. Eur Food Res Technol. 2010;230:865-874.*

Kobayashi et al. Supplementation of protein-free diet with whey protein hydrolysates prevents skeletal muscle mass loss in rats. Journal of Nutrition & Intermediary Metabolism. 2016;4:1-5.*

Shimoto, Hidesato, "Advanced hydrolysis of proteins using proteolytic enzymes" Special Feature II/Food Development using enzymes 2, *Department of Applied Technology, Novo Nordisk Bioindustry Co., Ltd.*, Dec. 31, 1996, (14 pages in English, 3 pages in Japanese).

Suh, Hyung Joo, et al. "Optimal Enzyme Selection for Organic Whey Protein Hydrolysis." *The Korean Journal of Food and Nutrition* vol. 30 No. 6 (Sep. 9, 2017): pp. 1359-1363.

* cited by examiner

*Primary Examiner* — Lynn Y Fan
(74) *Attorney, Agent, or Firm* — NSIP Law

(57) ABSTRACT

The present disclosure relates to a composition for alleviating, preventing or treating sarcopenia, containing, as an active ingredient, a whey protein hydrolysate, obtained by performing, on whey protein, primary hydrolysis using a *Bacillus licheniformis*-derived endoprotease and secondary hydrolysis using an *Aspergillus oryzae*-derived exoprotease, which inhibits protein degradation and activates protein synthesis through the PI3K-Akt pathway, thereby reducing muscle loss and increasing muscle size and muscle strength.

10 Claims, 26 Drawing Sheets

Specification includes a Sequence Listing.

Example 1

Comparative Example 3

| | 0μg/mL | 50μg/mL | 100μg/mL | 250μg/mL | 500μg/mL |
|---|---|---|---|---|---|
| ■MEAN | 1.00 | 0.97 | 0.97 | 0.97 | 1.01 |
| STD | 0.05 | 0.06 | 0.06 | 0.06 | 0.03 |

Comparative Example 4

| | 0 | 50μg/ml | 100μg/ml | 250μg/ml | 500μg/ml |
|---|---|---|---|---|---|
| ■MEAN | 1.00 | 0.94 | 0.94 | 0.94 | 0.92 |
| STD | 0.05 | 0.08 | 0.12 | 0.06 | 0.02 |

Comparative Example 5

COMPOSITION FOR ALLEVIATING, PREVENTING OR TREATING SARCOPENIA, CONTAINING WHEY PROTEIN HYDROLYSATE AS ACTIVE INGREDIENT

CROSS REFERENCE TO RELATED APPLICATIONS

This application is a U.S. National Stage Application of International Application No. PCT/KR2020/013116, filed on Sep. 25, 2020, which claims the benefit under 35 USC 119(a) and 365(b) of Korean Patent Application No. 10-2019-0118146, filed on Sep. 25, 2019 and Korean Patent Application No. 10-2020-0124083, filed on Sep. 24, 2020, in the Korean Intellectual Property Office, the entire disclosures of which are incorporated herein by reference for all purposes.

INCORPORATION-BY-REFERENCE OF MATERIAL SUBMITTED BY U.S.P.T.O. EFS-WEB

The instant application contains a Sequence Listing which is being submitted in computer readable form via the United States Patent and Trademark Office eFS-WEB system and which is hereby incorporated by reference in its entirety for all purposes. The txt file submitted herewith contains a 2,048 bytes file, which was created on Nov. 6, 2025 (EX20250919_J311410001_SeqListing.txt).

TECHNICAL FIELD

The present disclosure relates to a composition for alleviating, preventing or treating sarcopenia, which contains a whey protein hydrolysate as an active ingredient for increasing muscle size and muscle strength by reducing muscle loss.

BACKGROUND ART

Skeletal muscles are organs that constitute the largest part of the body. They account for 40-50% of the total body weight and play an important role in several metabolic functions including energy homeostasis, heat generation, etc. Human muscles decrease by 1% or more every year from 40 years old. At the age of 80 years, the muscle mass is decreased to about 50% of the maximum muscle mass. The muscle reduction in later life is considered the most important factor that lowers the overall body function. Change in muscles and fat mass, change in body shape such as skeletal distortion, etc. are perceived with aging. The prevalence of obesity in later life due to muscle loss is 30% or higher globally and is increasing gradually.

Because the disorder of insulin secretion can cause muscle development disorder due to insufficient energy supply to cells, the risk of sarcopenia is higher in diabetic patients than in normal people. In addition, since the muscle reduction increases arthritis, back pain and chronic pain and may aggravate urinary incontinence owing to abdominal obesity and fracture-induced injury can lead to death due to increased depression in later life, sarcopenia in later life is the major cause of lowering quality of life in connection with various diseases.

Sarcopenia is known to be closely related to senile chronic diseases such as osteoporosis, insulin resistance and arthritis. The decrease in physical activity caused by aging can be reduced by preventing or alleviating sarcopenia. The global market for treatment of progressive ataxia progressive ataxia and weakness disorder reached about 14 billion dollars in 2011 and has grown at a compound annual growth rate of 9.4% since then. It is expected to reach about 23.5 dollars in 2017.

Patients with sarcopenia show decrease in the number of myoblasts due to disorder of recruiting, activation or proliferation of satellite cells which are stem cells of myoblasts, and decreased proliferation and differentiation of myoblasts. Accordingly, the muscle of a patient with sarcopenia shows decreased number and size of muscle fibers at histological level and shows decreased muscle function.

With the active research on the epidemiology of sarcopenia in the US and Europe over the past 10 years, interest in the clinical importance of sarcopenia is soaring. Although the early researches mainly reported that sarcopenia lowers quality of life through general weakness, activity disorder and lack of muscle strength, recent studies showed that the risk of osteoporotic fracture can be increased remarkably. In addition, because sarcopenia induces chronic diseases such as diabetes, metabolic syndrome, obesity, chronic renal failure, chronic liver failure, etc. and ultimately leads to increased mortality, sarcopenia is attracting attentions as a disease to be treated properly.

Recently, it was reported that the risk of physical disability is increased by about 1.5-3.5 times in patients with sarcopenia in the US, causing annual social cost of 18.5 billion USD. According to the National Health and Nutrition Examination Survey of Korea, sarcopenia is a very common disease in Korea with a prevalence rate of 42.0% in men and 42.7% in women who are 60 years or older. It is certain that it will be an important social issue in Korea because the country has the world's fastest growing population.

Although it is known that exercise and protein and calorie supplement are helpful for sarcopenia, they are of little use for the elderly who account for most of the patients and the development of therapeutic agents is urgent. However, drugs that exhibit direct effect on alleviation of muscle reduction and increase of muscle mass are in clinical phases and no medication has been approved by FDA at present. Although there have been efforts to develop some selective androgen receptor modulators, activin receptor antagonists, fast skeletal muscle troponin inhibitors, etc. as therapeutic agents for sarcopenia, they are in early clinical phases at present.

According to a report on the trend of therapeutic agents for sarcopenia, it is predicted that the global sarcopenia therapeutics market will grow from about 10 million dollars (US) in 2010 to 20 million dollars (US) in 2018 ("Sarcopenia Therapeutics—Pipeline Assessment and Market Forecasts to 2018", 2011 Nov. 17). In addition, the Innovative Medicines Initiative which is a private conservation cooperative body under the EU announced in 2013 that the institute would invest about 50 million euros in the development of a therapeutic agent for senile sarcopenia as one of the four major health research issues, and the investment project is underway.

Thus, a therapeutic agent for sarcopenia using natural products that can be safely taken by the elderly for a long time is necessary.

DISCLOSURE

Technical Problem

The present disclosure is directed to providing a whey protein hydrolysate which increases muscle size and muscle strength by reducing muscle loss.

The present disclosure is also directed to providing a food composition for improving muscle function, which contains the whey protein hydrolysate as an active ingredient.

The present disclosure is also directed to providing a pharmaceutical composition for preventing or treating sarcopenia, which contains the whey protein hydrolysate as an active ingredient.

The present disclosure is also directed to providing a method for preparing the whey protein hydrolysate.

Technical Solution

A whey protein hydrolysate of the present disclosure may be obtained by performing, on whey protein, primary hydrolysis using a *Bacillus licheniformis*-derived endoprotease and secondary hydrolysis using an *Aspergillus oryzae*-derived exoprotease.

The whey protein may be derived from cheese whey.

The whey protein may be a normal whey powder, a demineralized whey powder, a whey protein concentrate or a whey protein isolate.

The whey protein hydrolysate may be a water-soluble whey protein hydrolysate with an insoluble substance removed.

The *Bacillus licheniformis*-derived endoprotease may be Alcalase, Protamex or a mixture enzyme thereof; and the *Aspergillus oryzae*-derived exoprotease may be Flavourzyme.

The mixture enzyme may be a mixture of Alcalase and Protamex at a weight ratio of 1:0.5-2.

The whey protein hydrolysate may consist of the following amino acids: 9-11 mg/g of Cys, 19-22 mg/g of Tyr, 18-19 mg/g of Arg, 37-39 mg/g of Ala, 43-45 mg/g of Pro, 68-72 mg/g of Lys, 13.5-14 mg/g of His, 40-41 mg/g of Ile, 77-80 mg/g of Leu, 15-17 mg/g of Met, 24-25 mg/g of Phe, 36-37 mg/g of Val, 120-130 mg/g of Glu, 80-82 mg/g of Asp, 35-41 mg/g of Ser, 14.5-15 mg/g of Gly, 54-55 mg/g of Thr and 10-11 mg/g of Trp.

The whey protein hydrolysate may include 1-5 wt % of free amino acids based on total amino acids.

The whey protein hydrolysate may include 155-180 mg/g of BCAA amino acids.

The content of indicator peptides of the whey protein hydrolysate may be 10-40 mg/g.

A food composition for improving muscle function of the present disclosure may contain a whey protein hydrolysate obtained by performing, on whey protein, primary hydrolysis using a *Bacillus licheniformis*-derived endoprotease and secondary hydrolysis using an *Aspergillus oryzae*-derived exoprotease as an active ingredient.

A food composition for alleviating or preventing sarcopenia of the present disclosure may contain a whey protein hydrolysate obtained by performing, on whey protein, primary hydrolysis using a *Bacillus licheniformis*-derived endoprotease and secondary hydrolysis using an *Aspergillus oryzae*-derived exoprotease as an active ingredient.

The sarcopenia may be muscular atrophy, myasthenia, muscular dystrophy, myotonia, hypotonia, muscle weakness, muscular atrophy, amyotrophic lateral sclerosis or myasthenia gravis.

In addition, a pharmaceutical composition for preventing or treating sarcopenia of the present disclosure may contain a whey protein hydrolysate obtained by performing, on whey protein, primary hydrolysis using a *Bacillus licheniformis*-derived endoprotease and secondary hydrolysis using an *Aspergillus oryzae*-derived exoprotease as an active ingredient.

The composition may increase muscle size.

The sarcopenia may be muscular atrophy, myasthenia, muscular dystrophy, myotonia, hypotonia, muscle weakness, muscular atrophy, amyotrophic lateral sclerosis or myasthenia gravis.

A method for preparing a water-soluble whey protein hydrolysate of the present disclosure may include: (A) a step of dissolving whey protein by mixing the whey protein with water at a weight ratio of 1:3-10; (B) a step of performing primary hydrolysis by adding 0.1-1 part by weight of a *Bacillus licheniformis*-derived endoprotease to 100 parts by weight of the dissolved whey protein; (C) a step of performing secondary hydrolysis by adding 0.1-1 part by weight of an *Aspergillus oryzae*-derived exoprotease to the primarily hydrolyzed hydrolysate; and (D) a step of obtaining a water-soluble whey protein hydrolysate by filtering the secondarily hydrolyzed hydrolysate to remove an insoluble substance.

The method may further include, after the step (D), (E) a step of sterilizing the obtained water-soluble whey protein hydrolysate and then cooling at room temperature; and (F) a step of drying and filtering the sterilized and cooled water-soluble whey protein hydrolysate.

The *Bacillus licheniformis*-derived endoprotease may be Alcalase, Protamex or a mixture enzyme thereof.

The *Aspergillus oryzae*-derived exoprotease may be Flavourzyme.

Advantageous Effects

A whey protein hydrolysate of the present disclosure and a composition containing the same as an active ingredient induce muscle hypertrophy and improve muscle function. In addition, because they increase the expression of muscle loss-associated genes as compared to a control group, the present disclosure can increase muscle size and muscle strength by reducing muscle loss.

In particular, the present disclosure can significantly increase muscle size and muscle strength because they express muscle synthesis-associated genes at a level similar to that of a normal group.

BEST MODE

Figure 1:
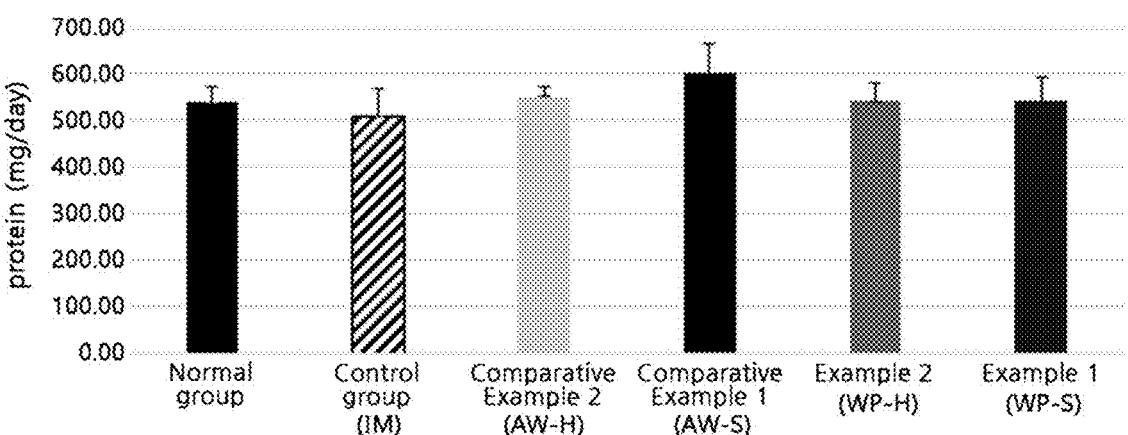
FIG. 1 shows the content of proteins supplied to a normal group, a control group, an Example 1 administration group, an Example 2 administration group, a Comparative Example 1 administration group and a Comparative Example 2 administration group.

The present disclosure relates to a composition for alleviating, preventing or treating sarcopenia, which contains a whey protein hydrolysate as an active ingredient for increasing muscle size and muscle strength by reducing muscle loss.

The whey protein used in the present disclosure is derived from cheese whey which is prepared during preparation of cheese from milk proteins by separating curd.

The whey protein may be a normal whey powder, a demineralized whey powder, a whey protein concentrate or a whey protein isolate.

Hereinafter, the present disclosure is described in detail.

The whey protein hydrolysate of the present disclosure is obtained by performing, on whey protein, primary hydrolysis using a *Bacillus licheniformis*-derived endoprotease and secondary hydrolysis using an *Aspergillus oryzae*-derived exoprotease.

The whey protein hydrolysate of the present disclosure may be specifically a water-soluble whey protein hydrolysate with an insoluble substance removed through filtering, although it is not specially limited as long as it is one obtained by degrading whey protein using a protease.

Specifically, the *Bacillus licheniformis*-derived endoprotease for performing primary hydrolysis on the whey protein may be Alcalase having an optimum protein degradation pH of 7.0-8.5, Protamex having an optimum protein degradation pH of 5.0-11.0 and an optimum temperature of 60° C., or Foodpro alkaline protease having an optimum protein degradation pH of 8.0-12.0 and an optimum temperature of 40-50° C. In addition, the *Aspergillus oryzae*-derived exoprotease for performing secondary hydrolysis may be Flavourzyme or Prozyme 2000P having an optimum protein degradation pH of 5.0-7.0 and an optimum temperature of 50° C. When other proteases are used, the effect of alleviating, preventing or treating sarcopenia may be low or nonexistent.

The whey protein hydrolysate hydrolyzed with the protease consists of the following amino acids: 9-11 mg/g of Cys, 19-22 mg/g of Tyr, 18-19 mg/g of Arg, 37-39 mg/g of Ala, 43-45 mg/g of Pro, 68-72 mg/g of Lys, 13.5-14 mg/g of His, 40-41 mg/g of Ile, 77-80 mg/g of Leu, 15-17 mg/g of Met, 24-25 mg/g of Phe, 36-37 mg/g of Val, 120-130 mg/g of Glu, 80-82 mg/g of Asp, 35-41 mg/g of Ser, 14.5-15 mg/g of Gly, 54-55 mg/g of Thr and 10-11 mg/g of Trp.

In addition, the whey protein hydrolysate of the present disclosure may include 1-5 wt %, specifically 2-3 wt %, of free amino acids based on total amino acids; and may include 155-180 mg/g, specifically 155-170 mg/g, of BCAA amino acids which refer to leucine (Leu), isoleucine (Ile) and valine (Val).

A superior effect of alleviating, preventing or treating sarcopenia may be achieved when the contents of free amino acids and BCAA amino acids based on total amino acids satisfy the ranges described above.

In addition, the whey protein hydrolysate of the present disclosure has a molecular weight of 100-5000 Da, specifically 200-3500 Da.

In addition, the whey protein hydrolysate of the present disclosure has an indicator peptide content of 10-40 mg/g, specifically 10-20 mg/g.

Because the whey protein hydrolysate of the present disclosure has a superior effect of alleviating, preventing or treating sarcopenia, it may be used as a food composition for improving muscle function or a food composition for alleviating or preventing sarcopenia and may also be used as a pharmaceutical composition for preventing or treating sarcopenia.

In the present specification, the term "sarcopenia" refers to a disease wherein muscle mass and muscle strength decline gradually. The sarcopenia may include muscular atrophy, myasthenia, muscular dystrophy, myotonia, hypotonia, muscle weakness, muscular atrophy, amyotrophic lateral sclerosis or myasthenia gravis.

In addition, in the present specification, the term "improvement of muscle function" means the effect of increasing muscle strength and/or size.

In addition, the present disclosure provides a method for preparing a water-soluble whey protein hydrolysate.

The method for preparing a water-soluble whey protein hydrolysate of the present disclosure includes: (A) a step of dissolving whey protein by mixing the whey protein with water at a weight ratio of 1:3-10; (B) a step of performing primary hydrolysis by adding 0.1-1 part by weight of a *Bacillus licheniformis*-derived endoprotease to 100 parts by weight of the dissolved whey protein; (C) a step of performing secondary hydrolysis by adding 0.1-1 part by weight of an *Aspergillus oryzae*-derived exoprotease to the primarily hydrolyzed hydrolysate; and (D) a step of obtaining a water-soluble whey protein hydrolysate by filtering the secondarily hydrolyzed hydrolysate to remove an insoluble substance.

The method may further include, after the step (D), (E) a step of sterilizing the obtained water-soluble whey protein hydrolysate and then cooling at room temperature; and (F) a step of drying and filtering the sterilized and cooled water-soluble whey protein hydrolysate.

First, in the step (A), whey protein is dissolved by mixing the whey protein with water at a weight ratio of 1:3-10 at pH 7.0-7.5 and 40-60° C., specifically 50-55° C.

If the temperature and pH are out of the above ranges during the dissolution of the whey protein, the whey protein may not be dissolved.

Then, in the step (B), primary hydrolysis is performed by adding a *Bacillus licheniformis*-derived endoprotease to the dissolved whey protein.

The *Bacillus licheniformis*-derived endoprotease may be a mixture of two different *Bacillus licheniformis*-derived endoproteases, more specifically a mixture enzyme of Alcalase and Protamex.

The Alcalase and the Protamex are mixed at a weight ratio of 1:0.5-2, specifically 1:1-1.5. If the content of the Protamex with respect to the Alcalase is outside the above range, the effect of alleviating, preventing or treating sarcopenia may be decreased.

If the mixture enzyme of Alcalase and Protamex is used, the protein is degraded from the inside of the chain. Therefore, the protein is degraded sparsely and medium-sized peptides, particularly hydrophobic peptides, are exposed at the end portion, leading to decline in sensory preference due to strongly bitter taste. Therefore, secondary hydrolysis is performed in the next step using a second protease to improve this problem.

In addition, the mixture enzyme of Alcalase and Protamex is used in an amount of 0.1-1 part by weight, specifically 0.1-0.4 part by weight, based on 100 parts by weight of the dissolved whey protein. When the content of the mixture enzyme is below the lower limit, short-length peptides may not be produced in large quantities. And, if the content exceeds the upper limit, the effect of alleviating, preventing or treating sarcopenia may be decreased as medium-length peptides are produced in large quantities.

In addition, the primary hydrolysis is performed at 40-60° C., specifically at 45-55° C., for 2-5 hours, specifically for 3-4 hours. If the reaction temperature and time during the primary hydrolysis are below the lower limits, the primary hydrolysis may not be performed completely. And, if they exceed the upper limits, byproducts may be produced in large quantities.

The primarily hydrolyzed hydrolysate has a pH of 6.0-7.0.

Then, in the step (C), secondary hydrolysis is performed by adding an *Aspergillus oryzae*-derived exoprotease to the primarily hydrolyzed hydrolysate.

Because the use of the mixture enzyme in the step (B) worsens sensory preference, the *Aspergillus oryzae*-derived exoprotease is used in the step (C) to produce shorter peptides and thus improve sensory preference.

The *Aspergillus oryzae*-derived exoprotease may be Flavourzyme.

The *Aspergillus oryzae*-derived exoprotease is added in an amount of 0.1-1 part by weight, specifically 0.2-0.5 part by weight, to 100 parts by weight of the dissolved whey protein. When the content of the second protease is below the lower limit, shorter peptides may be produced in smaller quantities. And, if the content exceeds the upper limit, byproducts may be produced in large quantities.

The secondary hydrolysis is performed at 40-60° C., specifically at 45-55° C., for 10-20 hours, specifically for 13-17 hours. If the reaction temperature and time during the secondary hydrolysis are below the lower limits, the secondary hydrolysis may not be performed completely. And, if they exceed the upper limits, byproducts may be produced in large quantities.

Then, in the step (D), a water-soluble whey protein hydrolysate is obtained by filtering the secondarily hydrolyzed hydrolysate to remove an insoluble substance. Before the step (D), the secondarily hydrolyzed hydrolysate is treated at 80-100° C. for 5-15 minutes for enzymatic deactivation and cooled to room temperature (23-26° C.). The cooled secondarily hydrolyzed hydrolysate is used in the step (D).

In the present disclosure, a water-soluble whey protein hydrolysate with an insoluble substance removed is obtained by filtering the secondarily hydrolyzed hydrolysate to achieve a better effect of alleviating, preventing or treating sarcopenia.

A hydrolysate without the insoluble substance removed has 3-20 times lower effect than the hydrolysate with the insoluble substance removed.

Specifically, the filtering may be performed using a housing filter although any method capable of removing the insoluble substance may be used without limitation.

Then, in the step (E), the obtained water-soluble whey protein hydrolysate is sterilized at 80-100° C. for 20-60 minutes and then cooled at room temperature.

Then, in the step (F), the cooled and sterilized water-soluble whey protein hydrolysate is dried and filtered.

After drying the water-soluble whey protein hydrolysate by spray drying and removing magnetic substances, a water-soluble whey protein hydrolysate is obtained finally by filtering through a 30-40 mesh filter.

Meanwhile, in the present specification, the term 'containing as an active ingredient' refers to an amount sufficient to achieve the effect of the whey protein hydrolysate. For example, the whey protein hydrolysate is used at a concentration of 10-1500 μg/mL, specifically 50-1000 μg/mL. Since the whey protein hydrolysate causes no side effect in the human body, the upper limit of the amount of the whey protein hydrolysate contained in the composition of the present disclosure may be adequately selected by those skilled in the art.

The pharmaceutical composition of the present disclosure may be prepared using a pharmaceutically suitable and physiologically acceptable adjuvant in addition to the active ingredient. As the adjuvant, an excipient, a disintegrant, a sweetener, a binder, a coating agent, a swelling agent, a lubricant, a glidant, a flavorant, etc. may be used.

For administration, the pharmaceutical composition may be formulated using one or more pharmaceutically acceptable carrier in addition to the above-described active ingredient.

The pharmaceutical composition may be formulated into a granule, a powder, a tablet, a coated tablet, a capsule, a suppository, a liquid, a syrup, a juice, a suspension, an emulsion, a medicinal drop, an injectable solution, etc. For example, for formulation into a tablet or a capsule, the active ingredient may be used in combination with an oral, non-toxic, pharmaceutically acceptable, inert carrier such as ethanol, glycerol, water, etc. In addition, if desired or necessary, a suitable binder, lubricant, disintegrant or coloring agent may also be included. A suitable binder includes natural sugar such as starch, gelatin, glucose or β-lactose, natural or synthetic gum such as corn sweetener, acacia, tragacanth or sodium oleate, sodium stearate, magnesium stearate, sodium benzoate, sodium acetate, sodium chloride, etc., although not being limited thereto. The disintegrant includes starch, methyl cellulose, agar, bentonite, xanthan gum, etc., although not being limited thereto.

When the composition is formulated as a liquid solution, one or more of saline, sterile water, Ringer's solution, buffered saline, albumin injection, dextrose solution, maltodextrin solution, glycerol and ethanol, which are sterilized and biocompatible, may be used as a pharmaceutically acceptable carrier. If necessary, other common additives such as an antioxidant, a buffer, a bacteriostat, etc. may be added. In addition, an injectable formulation such as an aqueous solution, a suspension, an emulsion, etc., a pill, a capsule, a granule or a tablet may be prepared by further adding a diluent, a dispersant, a surfactant, a binder or a lubricant.

The formulations may be prepared using the methods described in Remington's Pharmaceutical Science, Mack Publishing Company, Easton PA depending on the particular diseases or ingredients.

The pharmaceutical composition of the present disclosure may be administered orally or parenterally. For parenteral administration, it may be administered by intravenous injection, subcutaneous injection, intramuscular injection, intraperitoneal injection, transdermal administration, etc. Specifically, it may be administered orally.

An appropriate administration dosage of the pharmaceutical composition of the present disclosure varies factors such as formulation method, mode of administration, the age, body weight, sex, pathological condition and diet of a patient, administration time, administration route, excretion rate and response sensitivity, and an ordinarily skilled physician may easily determine and prescribe an administration dosage effective for desired treatment or prevention. According to a specific exemplary embodiment of the present disclosure, a daily administration dosage of the pharmaceutical composition of the present disclosure is 0.001-10 g/kg.

The pharmaceutical composition of the present disclosure may be prepared as a single-dose or multiple-dose unit using a pharmaceutically acceptable carrier and/or excipient. It may be formulated into a solution in an oily or aqueous medium, a suspension, an emulsion, an extract, a powder, a granule, a tablet or a capsule, and may further contain a dispersant or a stabilizer.

In addition, the present disclosure provides a food composition for alleviating, preventing or treating sarcopenia, which contains a whey protein hydrolysate as an active ingredient.

The food composition according to the present disclosure may be formulated by the same method as the pharmaceutical composition, and may be used as a functional food or added to various foods. The foods to which the composition of the present disclosure may be added include, for example, beverages, alcoholic beverages, confectionery, diet bar, dairy products, meat, chocolate, pizza, ramen, other noodles, gums, ice creams, vitamin complexes, dietary supplements, etc.

The food composition of the present disclosure may contain, in addition to the whey protein hydrolysate as an active ingredient, ingredients commonly added for preparation of food, e.g., proteins, carbohydrates, fats, nutrients, flavors and flavorants. Examples of the carbohydrates include common sugars such as monosaccharides, e.g., glucose, fructose, etc.; disaccharide, e.g., maltose, sucrose, oligosaccharide, etc.; and polysaccharides, e.g., dextrin, cyclodextrin, etc., and sugar alcohols such as xylitol, sorbitol, erythritol, etc. As the flavorants, natural flavorants (thaumatin or *Stevia* extract (e.g., rebaudioside A, glycyrrhizin, etc.)) or synthetic flavorants (saccharin, aspartame, etc.) may be used. For example, when the food composition of the present disclosure is prepared as a drink or a beverage, it may further contain citric acid, fructose syrup, sugar, glucose, acetic acid, malic acid, fruit juice, plant extract, etc. in addition to the whey protein hydrolysate of the present disclosure.

The present disclosure provides a functional health food for alleviating, preventing or treating sarcopenia, which includes the food composition containing a whey protein hydrolysate as an active ingredient. The functional health food refers to a food prepared by adding a whey protein hydrolysate to food materials such as beverages, teas, spices, gums, confectionery, etc. or prepared as a capsule, a powder, a suspension, etc., which provides a special health effect. Unlike general medicines, it is advantageous in that there is no side effect that may occur during long-term use of medicines. The functional health food of the present disclosure is very useful because it can be ingested routinely. The addition amount of the whey protein hydrolysate in the functional health food may vary depending on the type of the functional health food within a range not negatively affecting the inherent taste of the food. Usually, its content in the food is 0.01-50 wt %, specifically 0.1-20 wt %. When the functional health food is in the form of a pill, a granule, a tablet or a capsule, it may be added in an amount of usually 0.1-100 wt %, specifically 0.5-80 wt %. In a specific exemplary embodiment, the functional health food of the present disclosure may be in the form of a pill, a tablet, a capsule or a beverage.

In addition, the present disclosure provides a use of a whey protein hydrolysate for preparation of a medicine or a food for alleviating, preventing or treating sarcopenia. As described above, the whey protein hydrolysate may be used for alleviating, preventing or treating sarcopenia.

In addition, the present disclosure provides a method for alleviating, preventing or treating sarcopenia, which includes administering an effective amount of a whey protein hydrolysate to a mammal.

The term "mammal" used herein refers to a mammal which is the subject of treatment, observation or experiment, and specifically refers to human.

The term "effective amount" used herein refers to an amount of the active ingredient or the pharmaceutical composition sufficient to induce biological or medical response in tissues, an animal or human evaluated by researchers, veterinarians, medical doctors or clinical doctors, and includes an amount sufficient to alleviate the symptoms of a corresponding disease or disorder. The effective amount and administration number of the active ingredient of the present disclosure may be changed depending on the desired effect. Accordingly, the optimum administration dosage may be determined easily by those skilled in the art and may be adjusted depending on various factors including the type of a disease, the severity of the disease, the content of the active ingredient and other ingredients contained in the composition, the type of a formulation, the age, body weight, general health condition, sex and diet of a patient, administration time, administration route, the excretion rate of the composition, treatment period and co-administered drugs. Specifically, the administration dosage of the whey protein hydrolysate in the method for preventing, treating or alleviating of the present disclosure may be 0.001-10 g/kg/day.

In the treatment method of the present disclosure, the composition containing the whey protein hydrolysate as an active ingredient may be administered by common methods through oral, rectal, intravenous, intraarterial, intraperitoneal, intramuscular, intrasternal, transdermal, topical, intraocular or intradermal routes.

MODE FOR INVENTION

Hereinafter, specific examples will be presented to help understanding the present disclosure. However, the following examples only illustrate the present disclosure, and it will be obvious to those skilled in the art that various changes and modifications can be made thereto within the scope and technical idea of the present disclosure and such changes and modifications are encompassed within the scope of the appended claims.

Comparison of Water-Soluble Whey Protein Hydrolysate and Whey Protein Hydrolysate

Example 1. Water-Soluble Whey Protein Hydrolysate (WP-S)

After dissolving whey protein by mixing whey protein (WPC) with water at 50° C. at a weight ratio of 1:5 and adjusting pH to 7.0-7.5 using sodium bicarbonate, 0.4 part by weight of a mixture enzyme (Alcalase 2.4 L FG (Novo Nordisk):Protamex (Novo Nordisk)=1:1 weight ratio) was added to the dissolved whey protein 100 parts by weight and primary hydrolysis was performed at 50° C. for 4 hours. At the end of the primary hydrolysis, pH was 6.0-7.0.

After adding 0.2 part by weight of Flavourzyme 1000 L (Novo Nordisk) to the primarily hydrolyzed hydrolysate and performing secondary hydrolysis at 50° C. for 15 hours, a water-soluble whey protein hydrolysate was obtained by filtering the secondarily hydrolyzed hydrolysate through a housing filter (1 μm).

After sterilizing the obtained water-soluble whey protein hydrolysate at 90° C. for 30 minutes and then cooling at room temperature, followed by spray drying (inlet temperature: 190° C., outlet temperature: 100° C.; water evaporation rate: 1-3 kg/hr) and removal of impurities using a 10,000-gauss magnet, a water-soluble whey protein hydrolysate was obtained in powder form by filtering through a 40-mesh filter paper.

Example 2. Whey Protein Hydrolysate (WP-H)

A water-insoluble whey protein hydrolysate was obtained in the same manner as in Example 1, except that the secondarily hydrolyzed hydrolysate was used without being filtered through a housing filter.

Comparative Example 1. Water-Soluble Acidic Whey Protein Hydrolysate (AW-S)

A water-soluble acidic whey protein hydrolysate was obtained in the same manner as in Example 1, except that acidic whey protein was used instead of whey protein.

The acidic whey protein (acid whey) refers to whey protein isolated based on the isoelectric point through pH control rather than on mass difference.

Comparative Example 2. Acidic Whey Protein Hydrolysate (AW-H)

A water-insoluble acidic whey protein hydrolysate was obtained in the same manner as in Comparative Example 1, except that the secondarily hydrolyzed hydrolysate was used without being filtered through a housing filter.

Test Example I

Experimental Animals

It was investigated whether the hydrolysates prepared in the examples and comparative examples restore muscular atrophy in an animal model of muscular atrophy wherein muscular atrophy was induced in mice by hind limb immobilization (IM).

After conducting IM for a week, the four hydrolysates prepared in the examples and comparative examples were administered for 2 weeks while maintaining IM. Forty two 5-week-old male C57BL/6 mice were used in the experiment after accustomation to the laboratory environment for a week. Test groups were an untreated normal group (Normal), a control group (muscular atrophy-induced group, IM) and four hydrolysate administration groups (AW-H, AW-S, WP-H and WP-S), and each group consisted of seven mice. The sample was used after dissolving in clean water and was administered at a dosage of 800 mg/kg/day. The hind limb immobilization was performed by clamping one hind leg of the mouse using a device prepared with a 1.5-mL microtube, a clip and a Velcro tape according to the method described in the literature (Disease Models & Mechanisms, 8(9), 1059-1069, 2015). The diet and water intake and body weight of the mouse were measured with 3-day intervals throughout the experiment period.

—Six Test Groups—

Normal group (Normal): muscular atrophy was not induced.

Control group (IM): Water was administered instead of hydrolysate after inducing muscular atrophy.

Example 1 (WP-S): 800 mg/kg/day hydrolysate (WP-S) was administered inducing muscular atrophy.

Example 2 (WP-H): 800 mg/kg/day hydrolysate (WP-H) was administered inducing muscular atrophy.

Comparative Example 1 (AW-S): 800 mg/kg/day hydrolysate (AW-S) was administered inducing muscular atrophy.

Comparative Example 2 (AW-H): 800 mg/kg/day hydrolysate (AW-H) was administered inducing muscular atrophy.

Test Example 1. Measurement of Protein Content

FIG. 1 shows the content of proteins supplied to a normal group, a control group, an Example 1 administration group, an Example 2 administration group, a Comparative Example 1 administration group and a Comparative Example 2 administration group.

Because the supplied hydrolysate is a protein, daily protein intake was calculated from the amounts of diet intake and hydrolysate intake. As shown in FIG. 1, there was no significant difference between the groups in protein intake.

Test Example 2. Measurement of Change in Grip Strength

Figure 2:
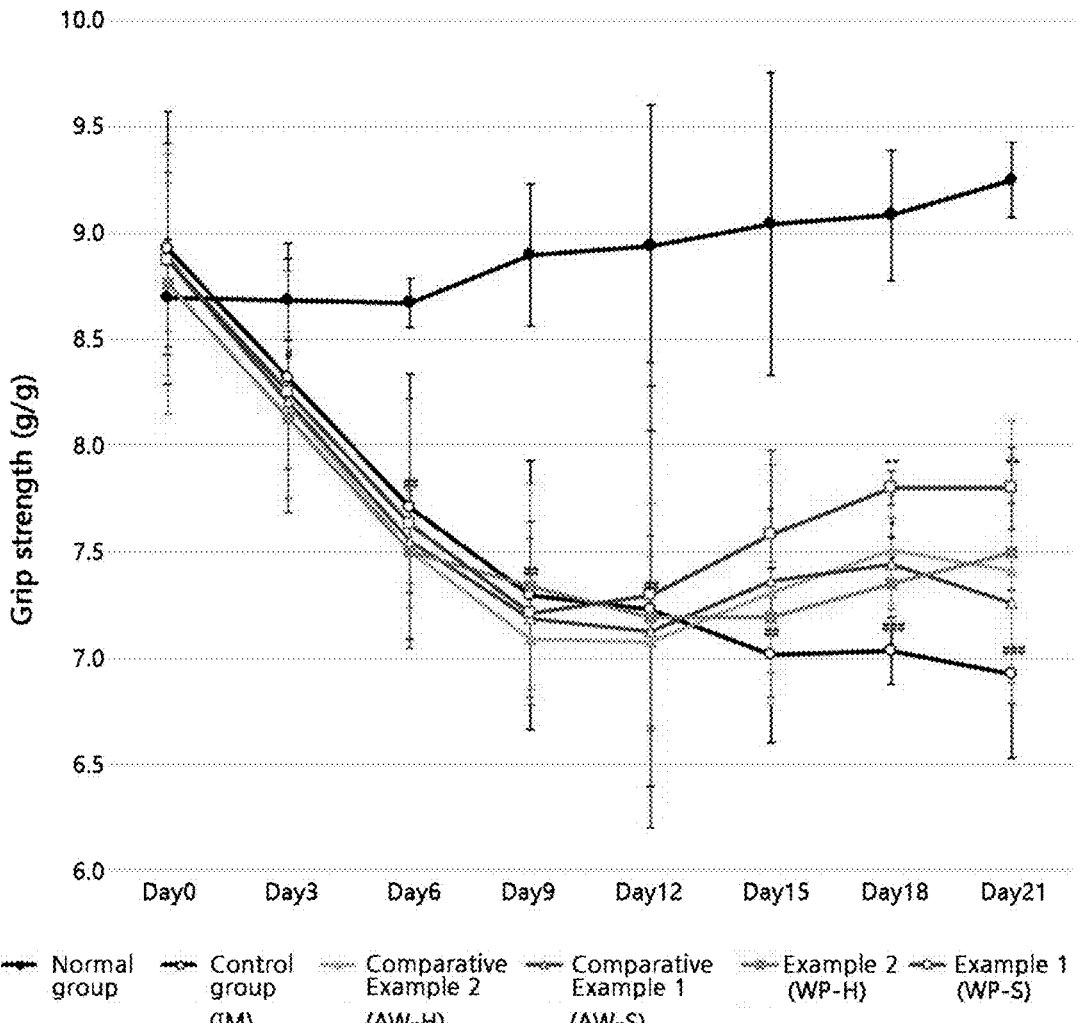
FIG. 2 shows the change in grip strength with time for a normal group, a control group, an Example 1 administration group, an Example 2 administration group, a Comparative Example 1 administration group and a Comparative Example 2 administration group.

FIG. 2 shows the change in grip strength with time for a normal group, a control group, an Example 1 administration group, an Example 2 administration group, a Comparative Example 1 administration group and a Comparative Example 2 administration group. $^{\#}P<0.05$, $^{\#\#}P<0.01$, $^{\#\#\#}P<0.001$.

During the period of hind limb immobilization and sample administration, the change in the grip strength of the mouse was measured with 3-day intervals using a grip strength meter (Bioseb, France). The mouse was held by the tail over the mesh of the grip strength meter and the maximum grip strength (g) was measured when any of the paws of the mouse was detached from the mesh. The Measurement was made 5 times per mouse and the mean value was recorded. The grip strength was normalized to body weight.

As shown in FIG. 2, the normal group showed increase in grip strength with time in proportion to the body weight. The control group showed significantly decreased grip strength as compared to the normal group.

In addition, it was confirmed that the Example 1 administration group showed significantly increased grip strength as compared to the normal group from day 9 after the oral administration of the hydrolysate.

In particular, the Example 1 administration group showed significantly increased grip strength as compared to other groups from day 12 after the oral administration of the hydrolysate.

Test Example 3. Measurement of Change in Muscle Tissue Weight

Figure 3A:
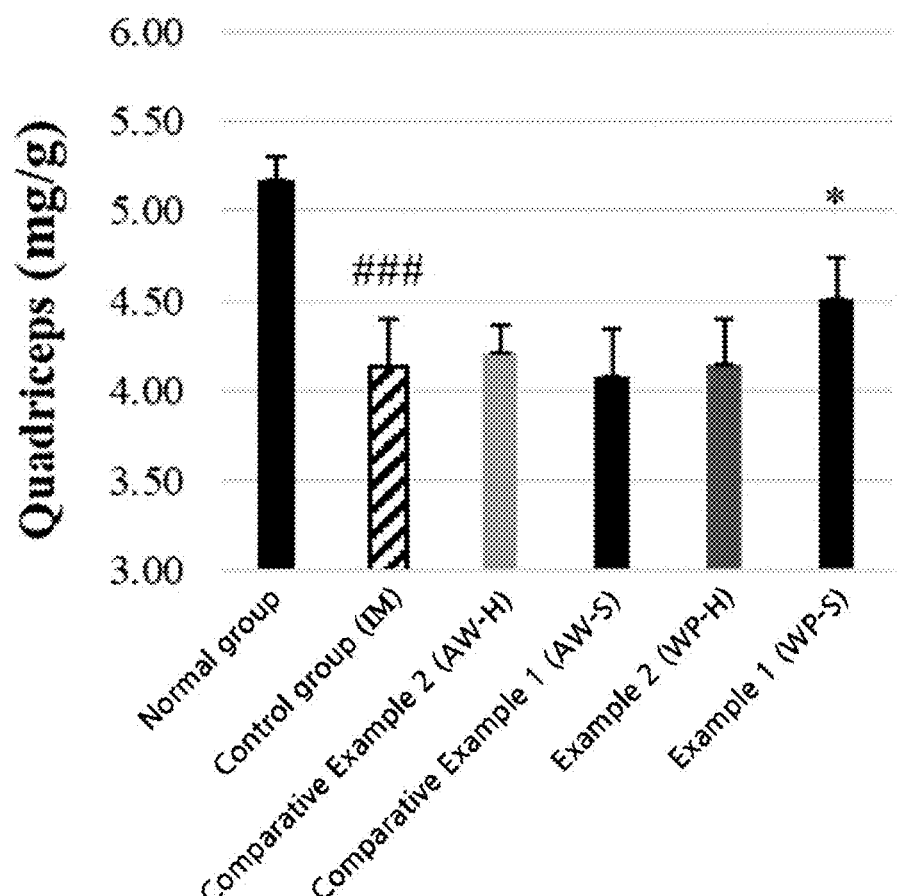
FIG. 3*a* shows a result of measuring the quadriceps weight of mice of a normal group, a control group, an Example 1 administration group, an Example 2 administration group, a Comparative Example 1 administration group and a Comparative Example 2 administration group.
Figure 3B:
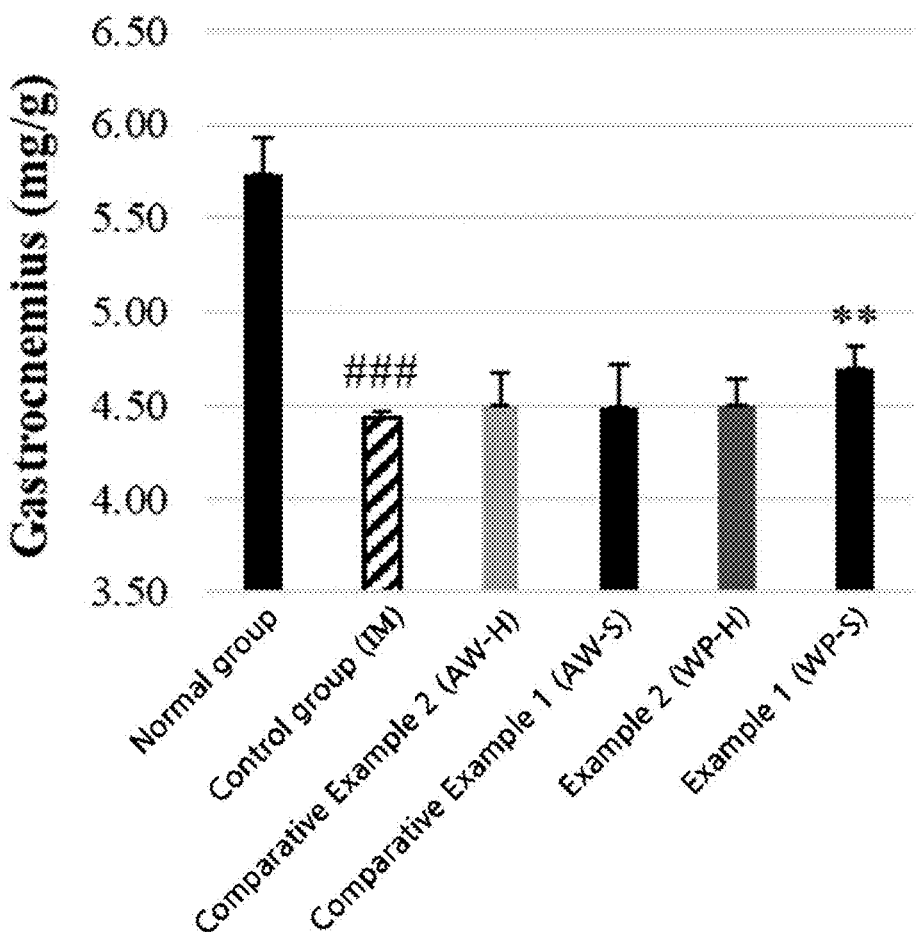
FIG. 3*b* shows a result of measuring the gastrocnemius weight of mice of a normal group, a control group, an Example 1 administration group, an Example 2 administration group, a Comparative Example 1 administration group and a Comparative Example 2 administration group.
Figure 3C:
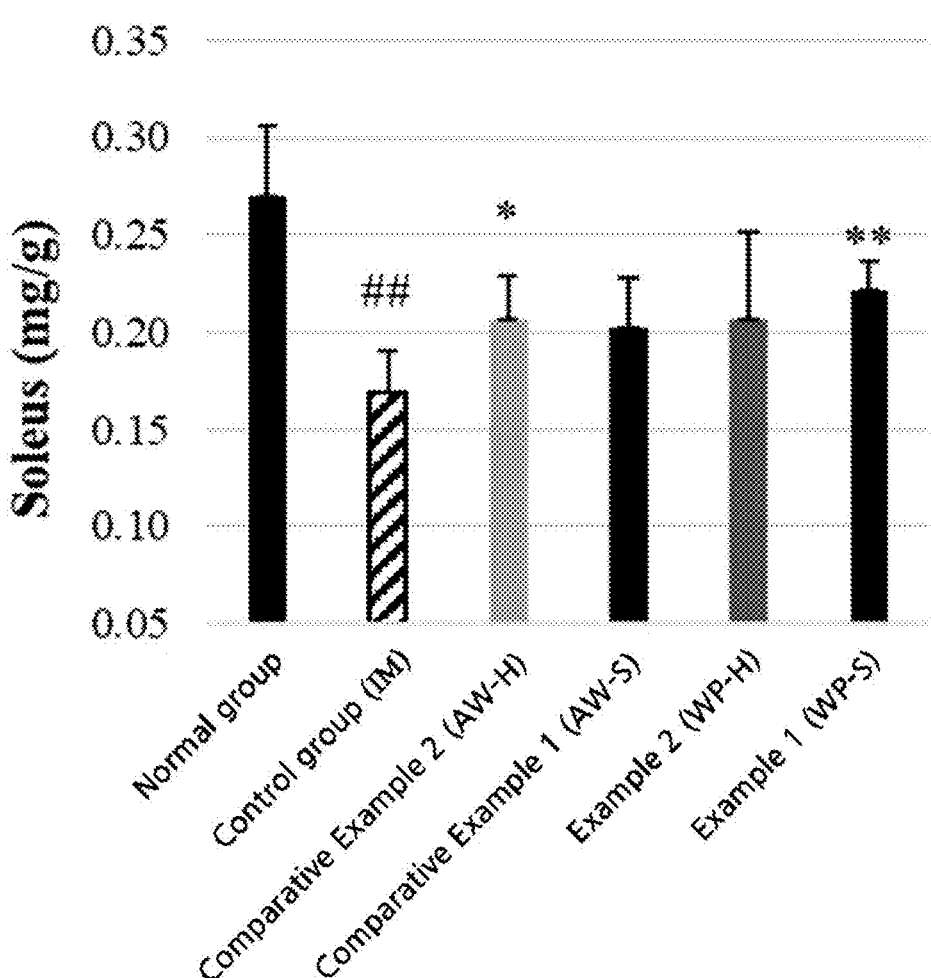
FIG. 3*c* shows a result of measuring the soleus weight of mice of a normal group, a control group, an Example 1 administration group, an Example 2 administration group, a Comparative Example 1 administration group and a Comparative Example 2 administration group.

FIG. 3a shows a result of measuring the quadriceps weight of the mice of a normal group, a control group, an Example 1 administration group, an Example 2 administration group, a Comparative Example 1 administration group and a Comparative Example 2 administration group; FIG. 3b shows a result of measuring the gastrocnemius weight of the mice of a normal group, a control group, an Example 1 administration group, an Example 2 administration group, a Comparative Example 1 administration group and a Comparative Example 2 administration group; and FIG. 3c shows a result of measuring the soleus weight of the mice of a normal group, a control group, an Example 1 administration group, an Example 2 administration group, a Comparative Example 1 administration group and a Comparative Example 2 administration group. $^{\#}P<0.05$, $^{\#\#}P<0.01$, $^{\#\#\#}P<0.001$.

The mouse was sacrificed and the weight of the quadriceps, gastrocnemius and soleus of one hind leg was measured. The measurement data were normalized to body weight and then compared.

As shown in FIG. 3, the weight of the quadriceps, the gastrocnemius and the soleus was decreased by about 20%, about 23% and about 37%, respectively, in the control group as compared to the normal group due to muscular atrophy.

It was confirmed that the weight of the quadriceps, the gastrocnemius and the soleus was decreased by about 13%, about 18% and about 18%, respectively, in the Example 1 (WP-S) administration group. That is to say, the muscle weight decrease was reduced by 36%, 20% and 52%, respectively.

In contrast, in the Comparative Example 2 (AW-H) administration group, the weight of the quadriceps, the gastrocnemius and the soleus was decreased by about 19%, about 22% and about 23%, respectively. That is to say, the muscle weight decrease was significantly reduced by 37%. In the Comparative Example 1 (AW-S) administration group, the weight of the quadriceps, the gastrocnemius and the soleus was decreased by about 21%, about 22% and about 25%, respectively, and in the Example 2 (WP-H) administration group, the weight of the quadriceps, the gastrocnemius and the soleus was decreased by about 20%, about 22% and about 23%, respectively.

Accordingly, it was confirmed that Example 1 (WP-S) showed the best effect of reducing muscle weight decrease among the four hydrolysates.

Figure 4:
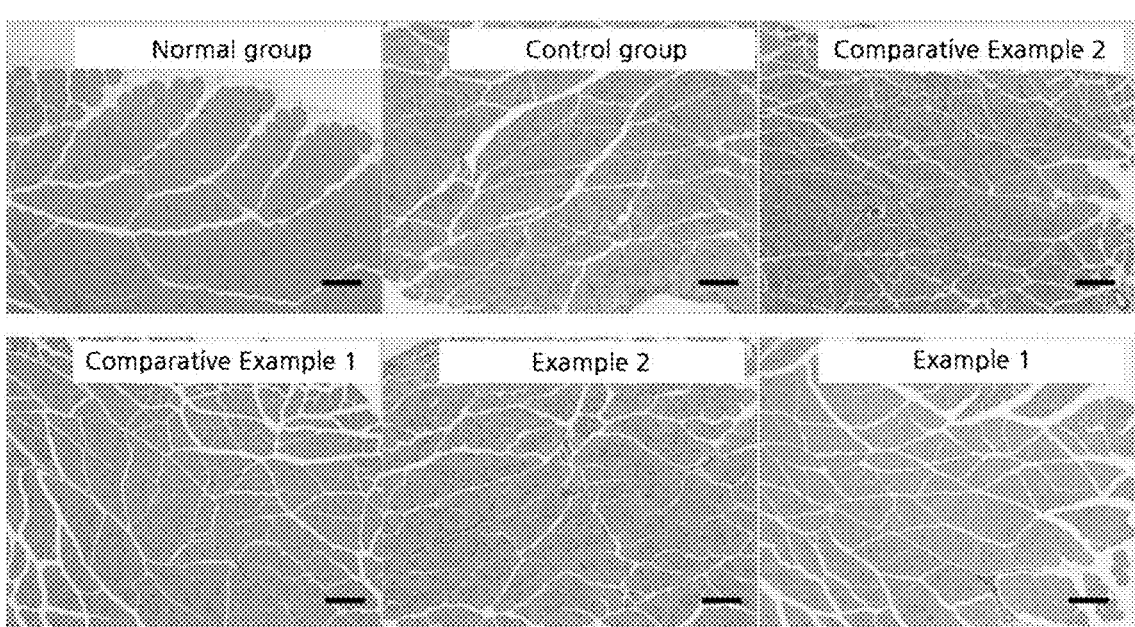
FIG. 4 shows the cross-sectional muscle fiber staining images for mice of a normal group, a control group, an Example 1 administration group, an Example 2 administration group, a Comparative Example 1 administration group and a Comparative Example 2 administration group.
Figure 5A:
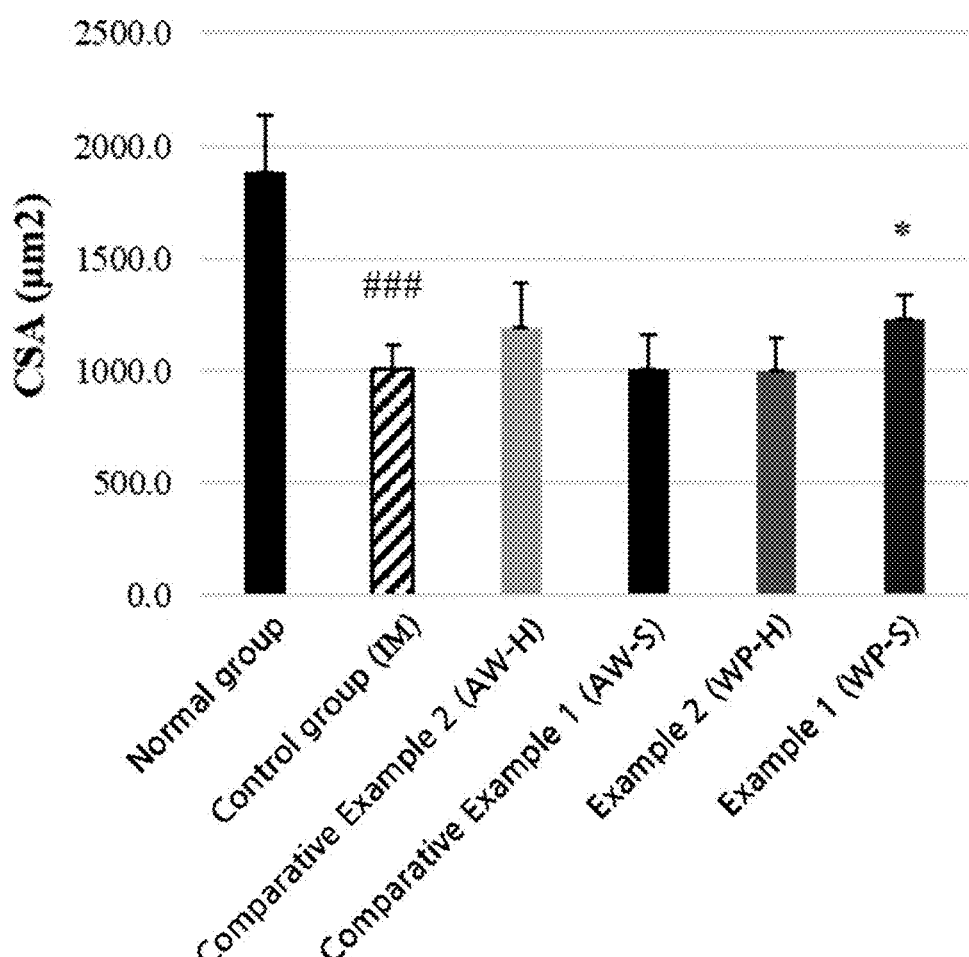
FIG. 5*a* shows a result of normalizing the cross-sectional muscle fiber staining images for mice of a normal group, a control group, an Example 1 administration group, an Example 2 administration group, a Comparative Example 1 administration group and a Comparative Example 2 administration group.
Figure 5B:
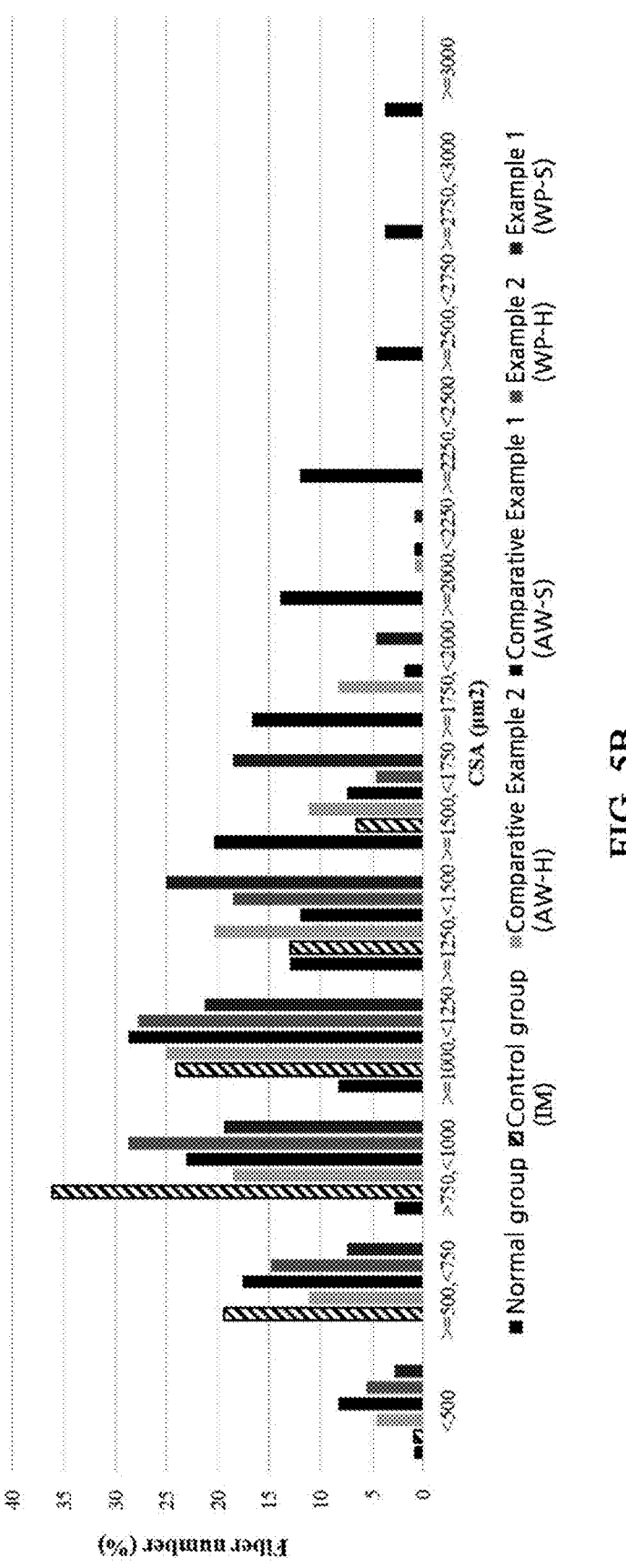
FIG. 5*b* shows the distribution of muscle fiber CSA in the muscle of mice of a normal group, a control group, an Example 1 administration group, an Example 2 administration group, a Comparative Example 1 administration group and a Comparative Example 2 administration group.

Test Example 4. Effect of Reducing Decrease of Cross-Sectional Area of Muscle Fiber FIG. 4 shows the cross-sectional muscle fiber staining images for the mice of a normal group, a control group, an Example 1 administration group, an Example 2 administration group, a Comparative Example 1 administration group and a Comparative Example 2 administration group; FIG. 5a shows a result of normalizing the cross-sectional muscle fiber staining images for the mice of a normal group, a control group, an Example 1 administration group, an Example 2 administration group, a Comparative Example 1 administration group and a Comparative Example 2 administration group; and FIG. 5b shows the distribution of muscle fiber CSA in the muscle of the mice of a normal group, a control group, an Example 1 administration group, an Example 2 administration group, a Comparative Example 1 administration group and a Comparative Example 2 administration group. $^{\#}P<0.05$, $^{\#\#}P<0.01$, $^{\#\#\#}P<0.001$.

Histological analysis was performed to investigate whether the hydrolysates improve the decrease of the cross-sectional area of muscle fibers in a mouse model of muscular atrophy. After fixing the gastrocnemius tissue obtained in Test Example 3 using 4% paraformaldehyde, the muscle tissue was sliced into 4-μm thick paraffin sections along a perpendicular direction to observe the cross-sectional area. The sections were stained with hematoxylin and eosin (H&E) for 13 hours and then observed with an optical microscope (Olympus, Tokyo, Japan) at ×100 magnification. Then, the cross-sectional area (CSA) of the muscle fiber was quantified using the ImageJ software.

As shown in FIGS. 4 and 5a-5b, the cross-sectional area of the muscle fiber was decreased by 47% in the control group as compared to the normal group due to muscular atrophy.

In addition, the cross-sectional area of the muscle fiber was decreased by about 37% in the Comparative Example 2 (AW-H) administration group, by about 47% in the Comparative Example 1 (AW-S) administration group, by about 47% in the Example 2 (WP-H) administration group and by about 34% in the Example 1 (WP-S) administration group, as compared to the normal group. It was confirmed that the decrease of the cross-sectional area of the muscle fiber was reduced significantly only in the Example 1 (WP-S) administration group by 25%.

When the number of muscle fibers was plotted against the cross-sectional area of the muscle fiber, the Example 1 (WP-S) administration group showed the closest distribution to the normal group.

Figure 6A:
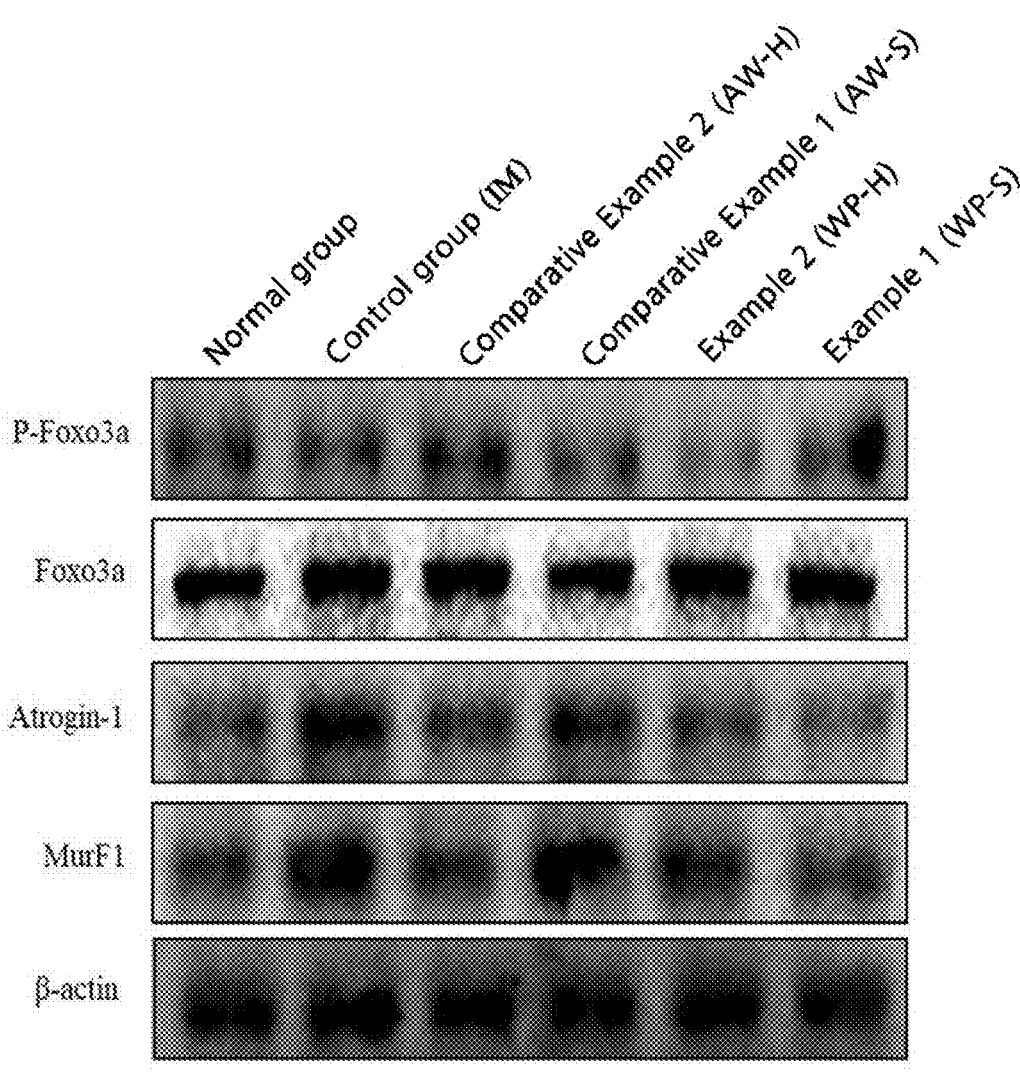
FIG. 6*a* shows a western blot result showing the expression of muscle degradation-associated factors in mice of a normal group, a control group, an Example 1 administration group, an Example 2 administration group, a Comparative Example 1 administration group and a Comparative Example 2 administration group.
Figure 6B:
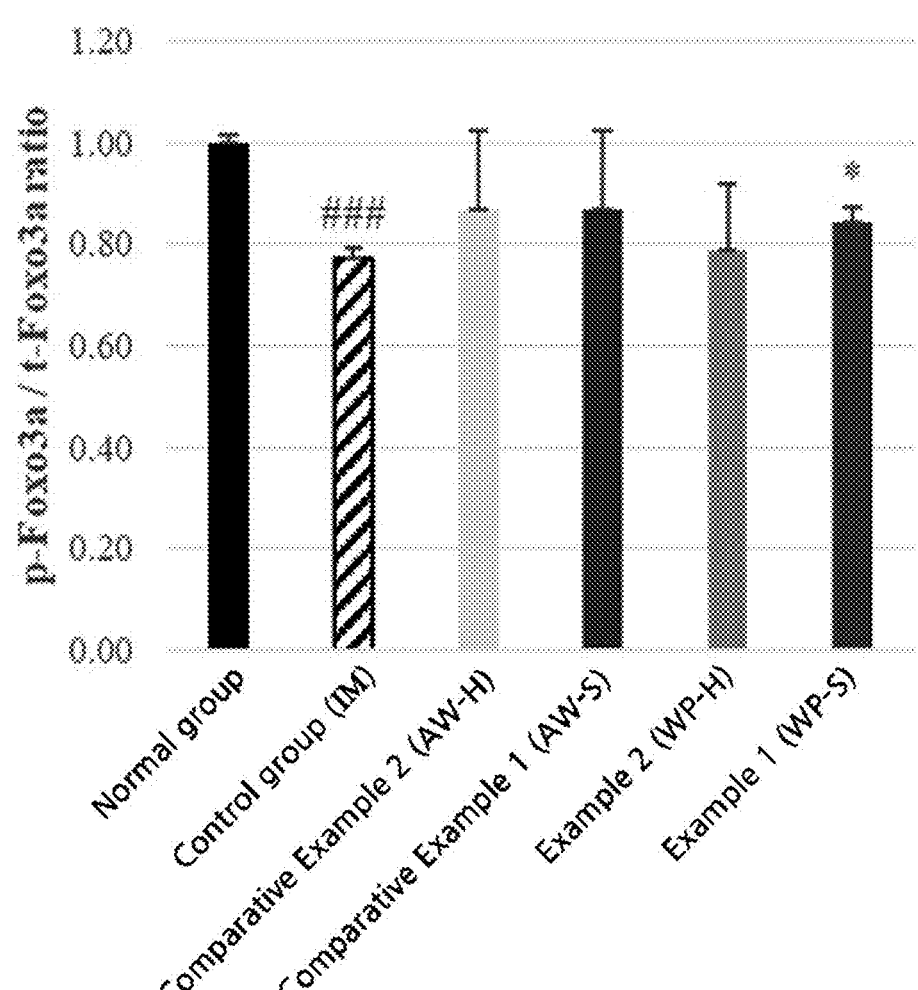
FIGS. 6*b*-6*g* respectively show the expression level of the factors p-Foxo3a, Atrogin-1 protein, MuRF-1 protein, Atrogin-1 mRNA, MuRF-1 mRNA and Bnip3 mRNA in mice of a normal group, a control group, an Example 1 administration group, an Example 2 administration group, a Comparative Example 1 administration group and a Comparative Example 2 administration group.
Figure 6C:
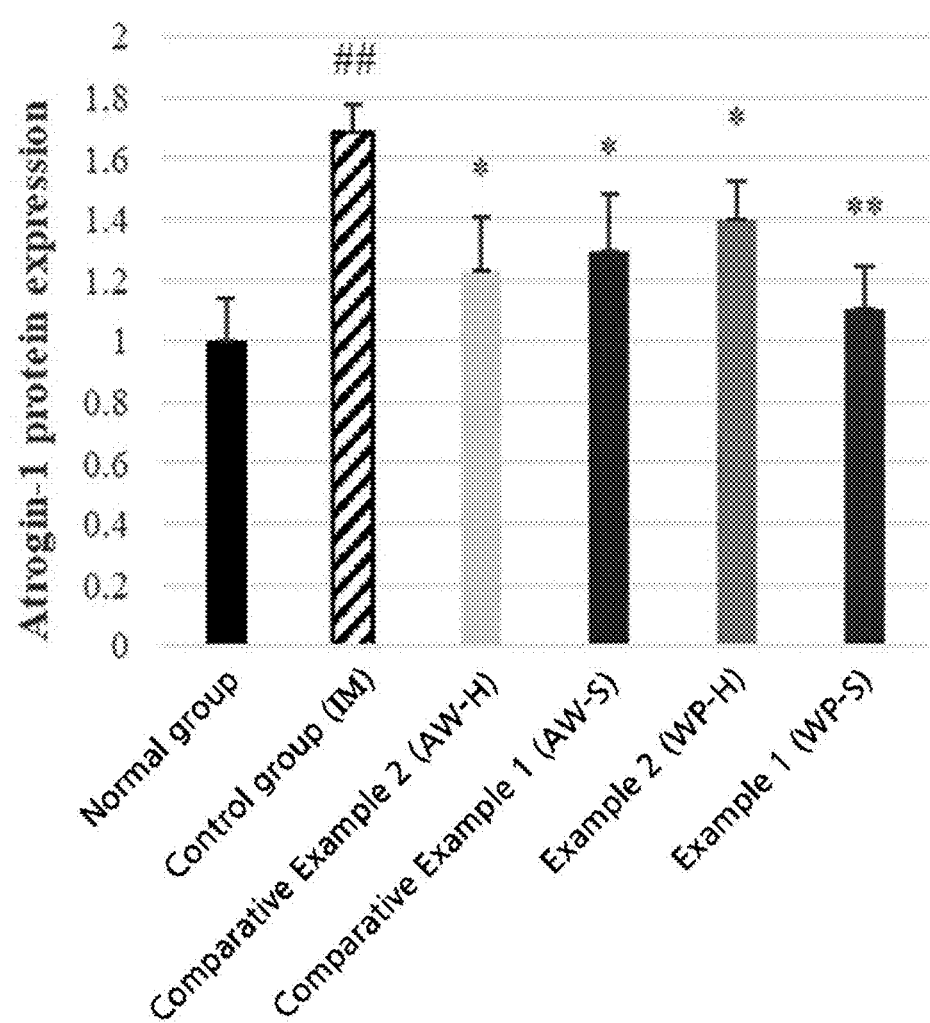
Figure 6D:
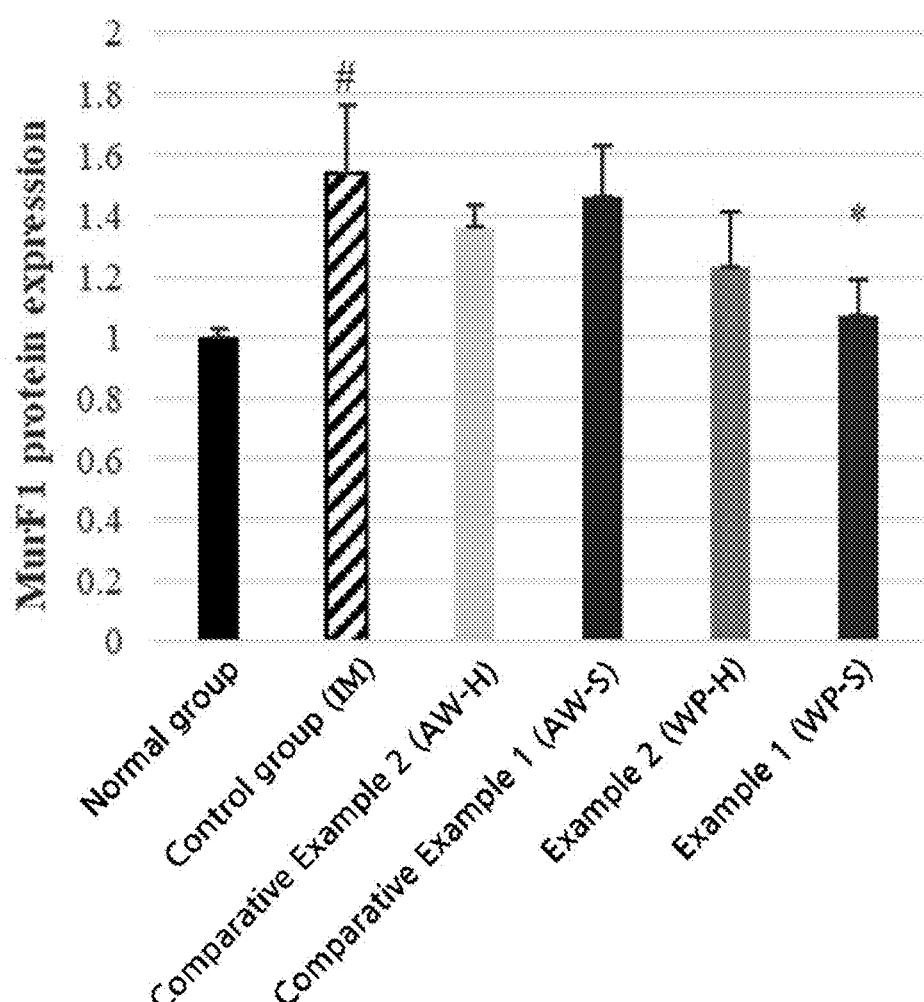
Figure 6E:
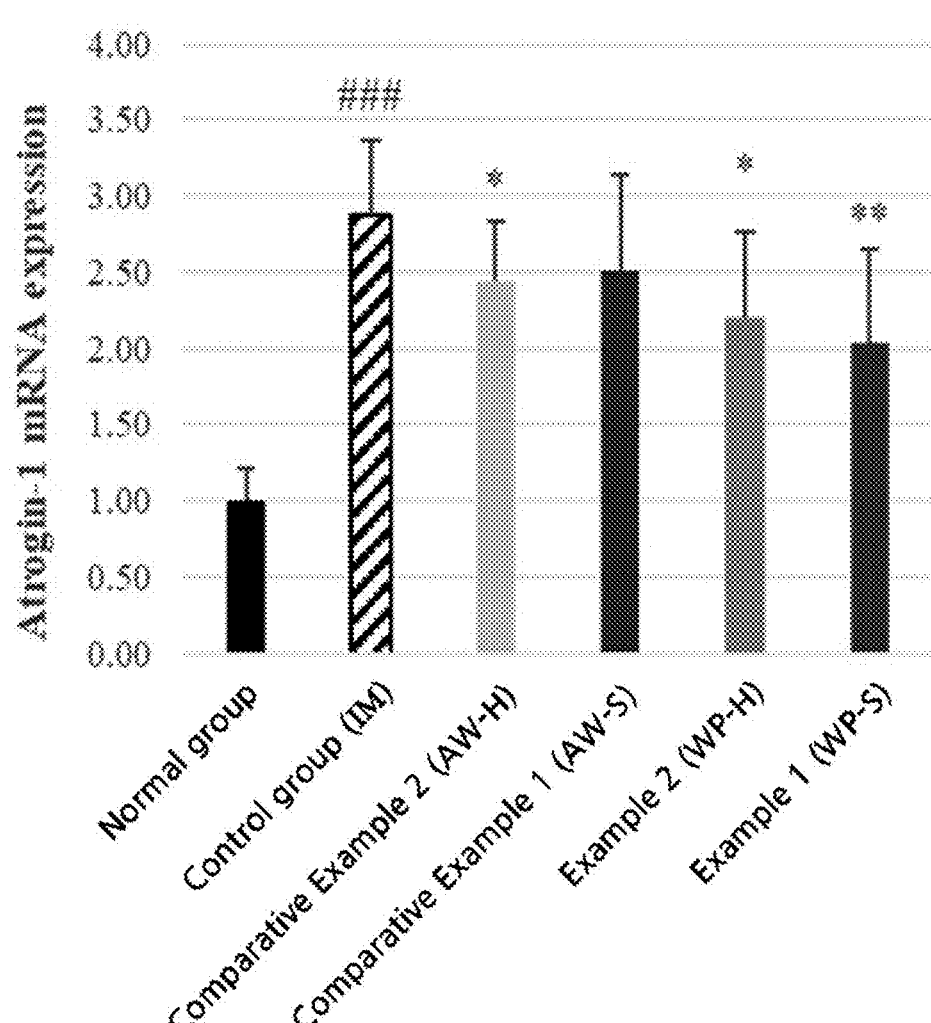
Figure 6F:
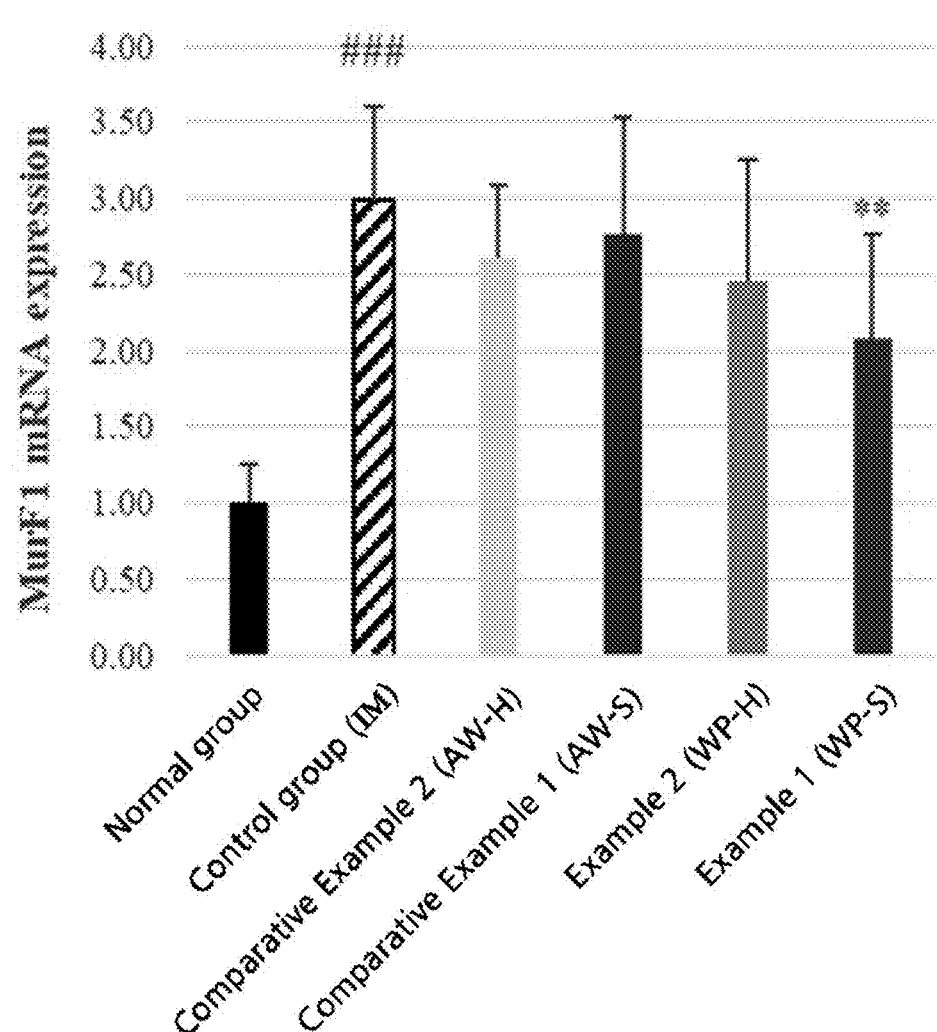
Figure 6G:
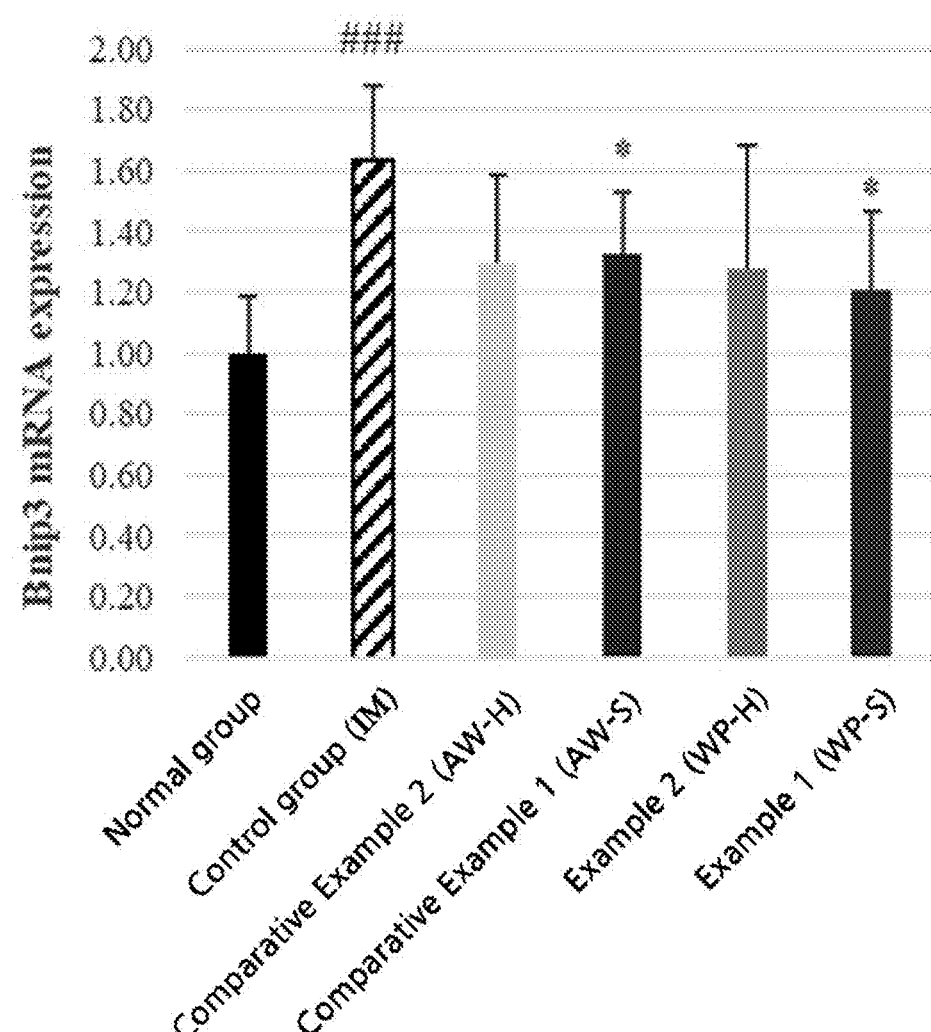

Test Example 5. Investigation of Regulation of Muscle Degradation-Associated Factors FIG. 6a shows a western blot result showing the expression of muscle degradation-associated factors in the mice of a normal group, a control group, an Example 1 administration group, an Example 2 administration group, a Comparative Example 1 administration group and a Comparative Example 2 administration group; and FIGS. 6b-6g respectively show the expression level of the factors p-Foxo3a, Atrogin-1 protein, MuRF-1 protein, Atrogin-1 mRNA, MuRF-1 mRNA and Bnip3 mRNA in the mice of a normal group, a control group, an Example 1 administration group, an Example 2 administration group, a Comparative Example 1 administration group and a Comparative Example 2 administration group. $^{\#}P<0.05$, $^{\#\#}P<0.01$, $^{\#\#\#}P<0.001$.

Western blot and qRT-PCR were conducted to investigate whether the protein and gene expression level of the muscle degradation-associated factors Foxo3a, MuRF-1, Atrogin-1 and Bnip3 are changed in a mouse model of muscular atrophy. Foxo3a is a muscular atrophy-related transcription factor. It is known that its activity is inhibited as it is localized in the cytosol when phosphorylated. Atrogin-1 and MuRF1 are ubiquitin ligases expressed specifically only in muscle. They are known as the most representative factors that degrade myoproteins in muscular atrophy. Bnip3 is a mitophagy- and autophagy-related factor. It is known that its expression is increased in muscular atrophy.

Proteins were extracted from the gastrocnemius taken in Test Example 3 using a lysis buffer containing Complete™ protease inhibitor cocktail tablets (Roche Diagnostics, Indianapolis, USA). After investigating the concentration of the extracted proteins using a Pierce™ BCA protein assay kit (Thermo Fisher Scientific, Rockford, USA) according to the manufacturer's instructions, the protein concentration was adjusted to a certain level. After electrophoresing the proteins on 12% sodium dodecyl sulfate (SDS)-polyacrylamide gel, they were transferred onto a polyvinylidene fluoride (PVDF) membrane by electroblotting. The membrane was blocked at room temperature for 1 hour using 5% skim milk and then incubated overnight at 4° C. with primary antibodies. Next day, the membrane was incubated with HRP (horseradish peroxidase)-conjugated secondary antibodies for 1.5 hours or longer and then developed using a LAS3000 luminescent image analyzer (Fuji Film, Tokyo, Japan). Foxo3a and p-Foxo3a antibodies were purchased from Cell Signaling Technology (Danvers, USA); MuRF-1 and Atrogin-1 secondary antibodies were purchased from Santa Cruz Biotechnology (Santa Cruz, USA); and β-actin antibody was purchased from GeneTex (California, USA).

After extracting mRNA from the gastrocnemius taken in Test Example 3 using easy-RED (iNtRON Biotechnology, Seongnam, Korea), cDNA was synthesized by reacting with 20 μL of a RevoScript™ Reverse Transcriptase premix kit (iNtRON Biotechnology). Then, Step One Plus real-time PCR (Applied Biosystems, CA, USA) was conducted using a mixture of 10 μL of SYBR premix EX Taq (Takara, Japan), 2 μL of cDNA, 1 μL of each primer (10 pmol/μL), 1 μL of a Rox dye and 6 μL of Rnase/Dnase free water. The primers were purchased from Bionics and their sequences are described in Table 1.

TABLE 1

| Oligo name | Primer sequence (5'- 3') |
| --- | --- |
| Atrogin1 F | SEQ ID NO: 1 |
| Atrogin1 R | SEQ ID NO: 2 |
| MurF1 F | SEQ ID NO: 3 |
| MurF1 R | SEQ ID NO: 4 |
| Bnip3 F | SEQ ID NO: 5 |
| Bnip3 R | SEQ ID NO: 6 |
| Gapdh F | SEQ ID NO: 7 |
| Gapdh R | SEQ ID NO: 8 |

As shown in FIGS. 6a-6g, the phosphorylation ratio of p-Foxo3a and Foxo3a were decreased significantly in the normal group as compared to the control group, and the ratio was increased significantly only in the Example 1 (WP-S) administration group.

In addition, the proteomic and genomic expression of Atrogin-1 was increased significantly in the control group as compared to the normal group, and the administration of the hydrolysates significantly decreased the expression (WP-S>AW-H≥WP-H).

In addition, the proteomic and genomic expression of MurF1 was increased significantly in the control group as compared to the normal group but was significantly decreased in the Example 1 (WP-S) administration group.

In addition, the genomic expression of Bnip3 was increased significantly in the control group as compared to the normal group, and the administration of the hydrolysates significantly decreased the expression (WP-S>AW-S).

In conclusion, the administration of Example 1 (WP-S) to the mouse model of muscular atrophy resolved muscular atrophy by decreasing the proteomic and genomic expression of muscle degradation-associated factors increased by muscular atrophy.

Figure 7A:
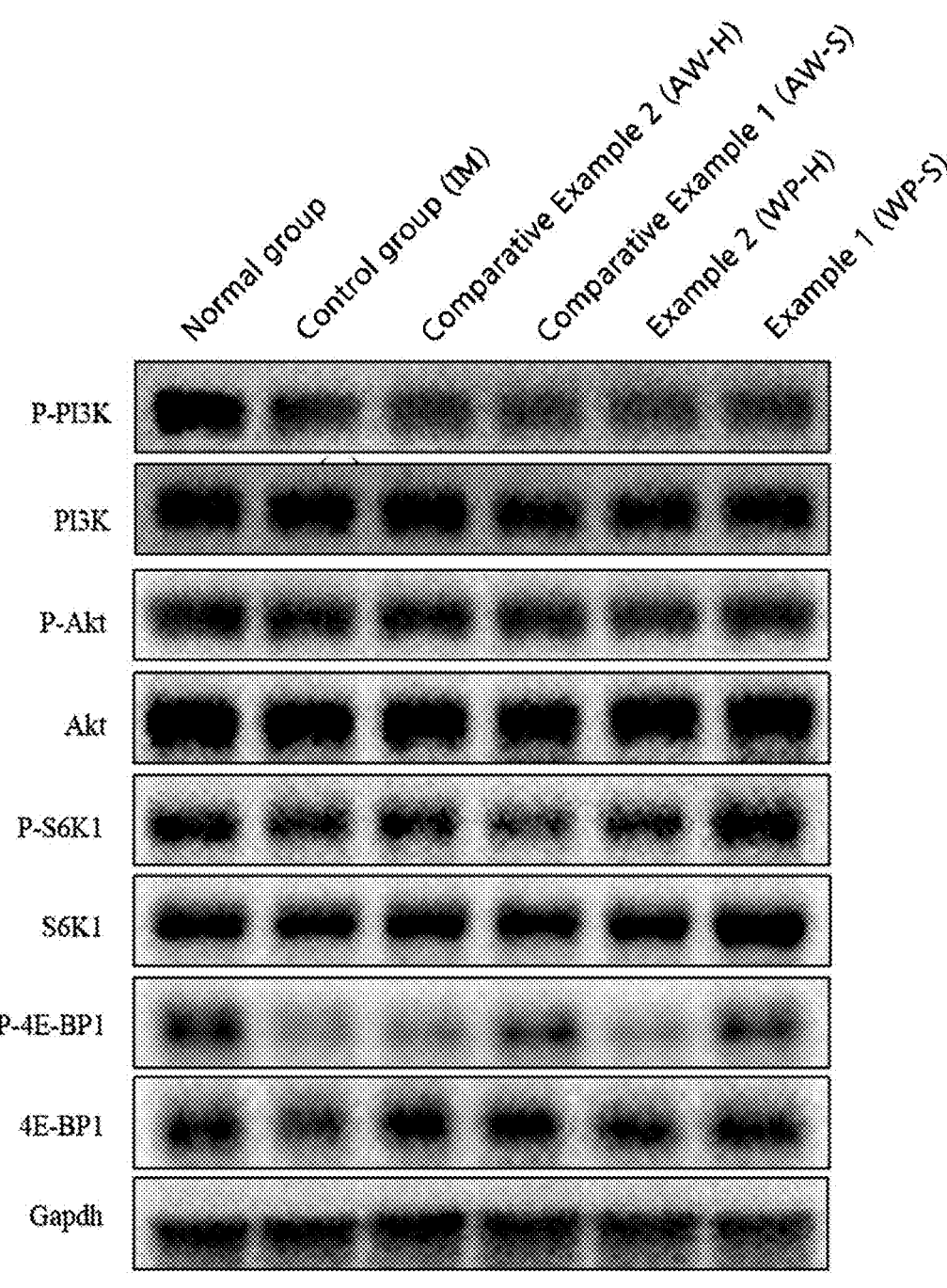
FIG. 7*a* shows a western blot result showing the expression of muscle synthesis-associated factors in mice of a normal group, a control group, an Example 1 administration group, an Example 2 administration group, a Comparative Example 1 administration group and a Comparative Example 2 administration group.
Figure 7B:
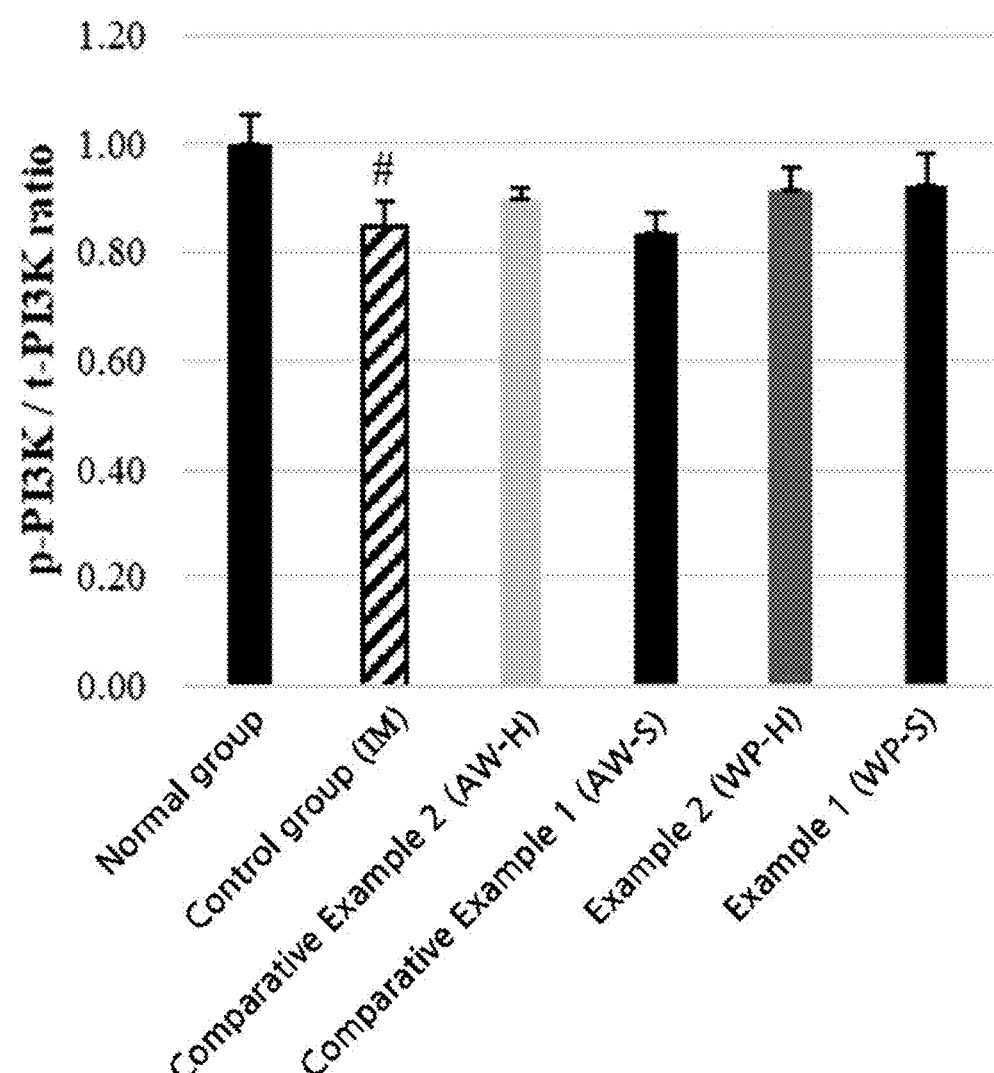
FIGS. 7*b*-7*e* show the phosphorylation ratio of the muscle synthesis-associated factors.
Figure 7C:
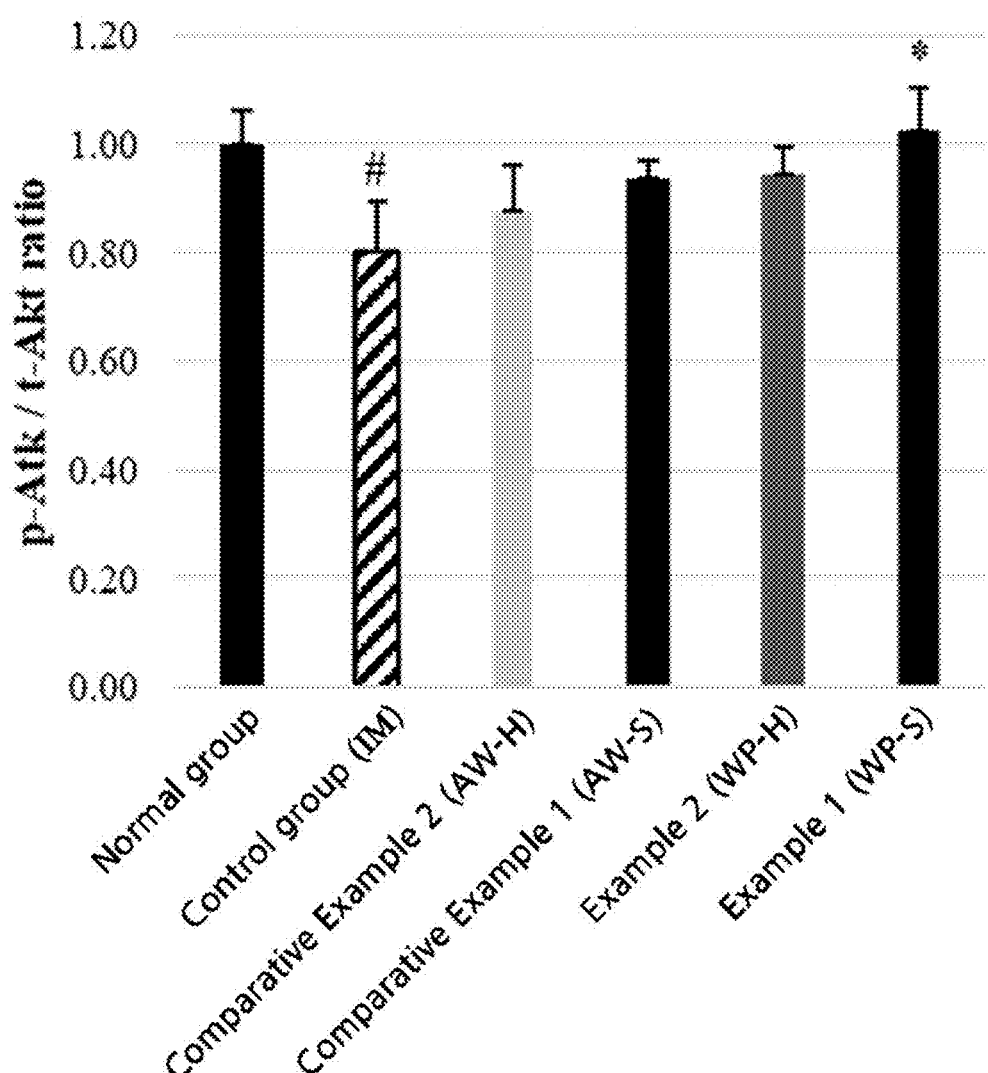
Figure 7D:
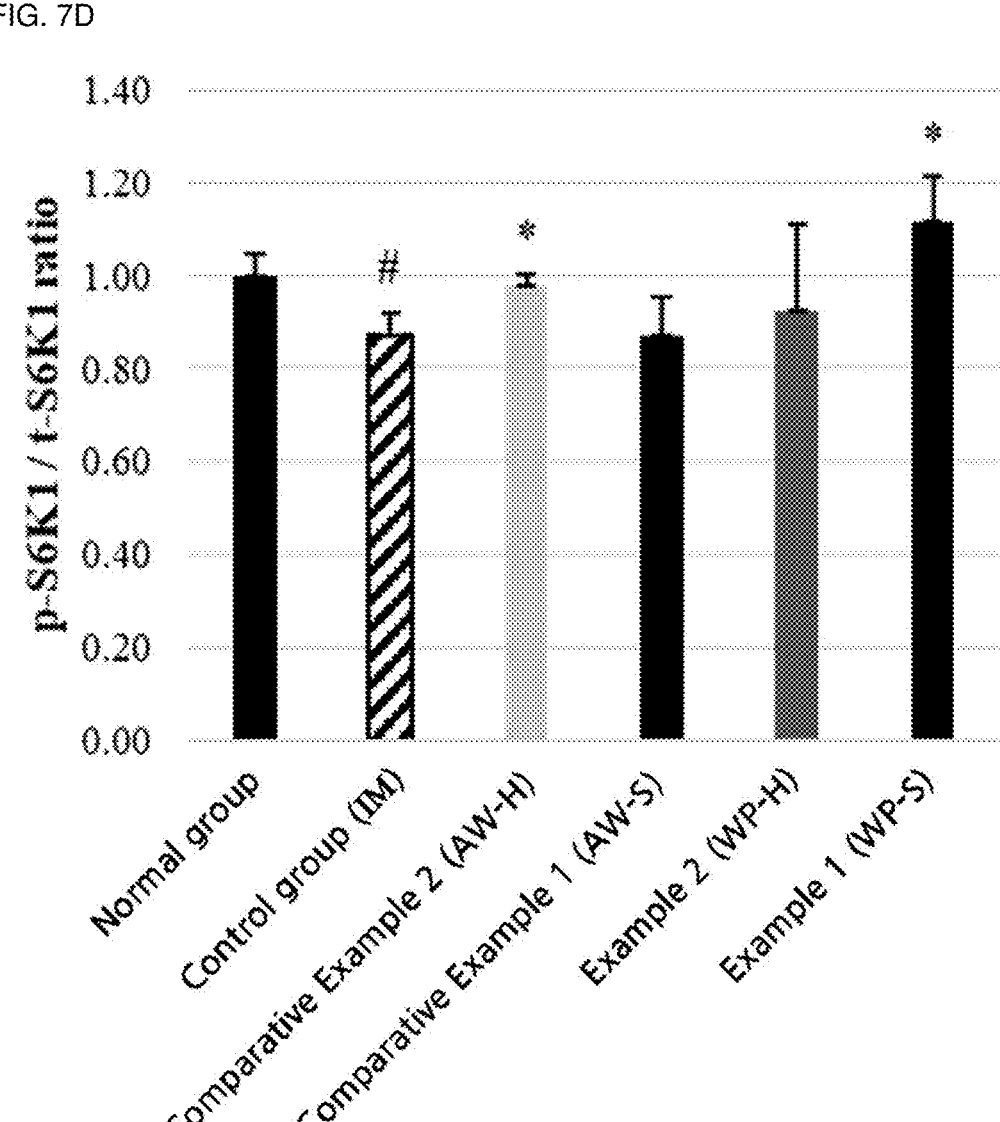
Figure 7E:
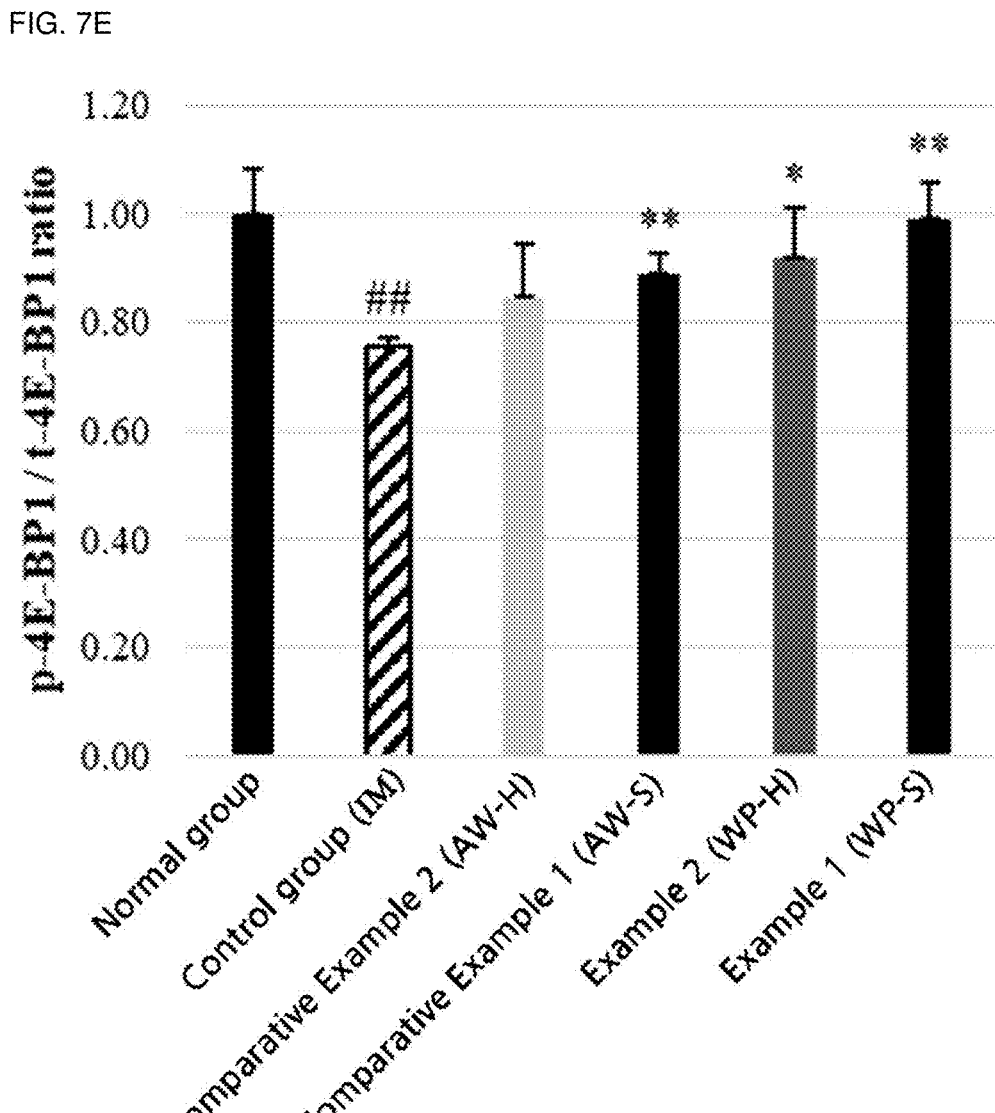

Test Example 6. Investigation of Regulation of Expression of Muscle Synthesis-Associated Factors FIG. 7a shows a western blot result showing the expression of muscle synthesis-associated factors in the mice of a normal group, a control group, an Example 1 administration group, an Example 2 administration group, a Comparative Example 1 administration group and a Comparative Example 2 administration group; and FIGS. 7b-7e show the phosphorylation ratio of the muscle synthesis-associated factors. $^{\#}P<0.05$, $^{\#\#}P<0.01$, $^{\#\#\#}P<0.001$.

Western blot was conducted to investigate whether the phosphorylation ratio of the muscle synthesis-associated factors PI3K, Akt, S6K1 and 4E-BP1 is changed in a mouse model of muscular atrophy. The PI3K-Akt pathway is known as a signaling pathway which is activated by growth factors such as IGF-1 and ultimately increases muscle synthesis. S6K1 and 4E-BP1 are phosphorylated by PI3K phosphorylation, Akt phosphorylation, etc., and protein synthesis is induced by phosphorylation of S6 ribosomal protein or release of eukaryotic translation initiation factor 4E (eIF4E). Therefore, the phosphorylation ratio of the four factors was measured by western blot to investigate whether muscle synthesis is increased by administration of the whey protein hydrolysates.

Western blot was conducted in the same manner as in Test Example 5 using the gastrocnemius taken in Test Example 3. p-PI3K antibody was purchased from Abcam (England); PI3K, p-Akt, Akt, p-S6K1, S6K1, p-4E-BP1 and 4E-BP1 antibodies were purchased from Cell Signaling Technology (Danvers, USA); and Gapdh antibody was purchased from GeneTex (California, USA).

As shown in FIG. 7, the phosphorylation ratio of p-PI3K and PI3K was decreased significantly in other groups as compared to the normal group.

In addition, the phosphorylation ratio of p-Akt and Akt was decreased significantly in the control group as compared to the normal group but was increased significantly by the administration of Example 1 (WP-S).

In addition, the phosphorylation ratio of p-S6K1 and S6K1 was decreased significantly in the control group as compared to the normal group but was increased significantly by the administration of the hydrolysates (WP-S>AW-H).

In addition, the phosphorylation ratio of p-4E-BP1 and 4E-BP1 was decreased significantly in the control group as compared to the normal group but was increased significantly by the administration of the hydrolysates (WP-S>WP-H>AW-S).

In conclusion, the administration of Example 1 (WP-S) to the mouse model of muscular atrophy resolved muscular atrophy by increasing the phosphorylation of muscle synthesis-associated factors decreased by muscular atrophy.

Comparison of Whey Protein Hydrolysate of the Present Disclosure with Other Whey Protein Hydrolysates

Example 1. Water-Soluble Whey Protein Hydrolysate (WP-S)

The water-soluble whey protein hydrolysate of Example 1 was used.

Comparative Example 3. Arla Whey Protein Hydrolysate

Arla whey protein hydrolysate (Arla Foods Ingredients, Arla SP-8011) was used.

Comparative Example 4. Hilmar Whey Protein Hydrolysate

Hilmar whey protein hydrolysate (Hilmar Ingredients, Hilmar 8010) was used.

Comparative Example 5. Murray Goulburn Whey Protein Hydrolysate

Murray Goulburn whey protein hydrolysate (Example 2 in Korean Patent Registration No. 1311318) was used.

Test Example II

Test Example 7. Measurement of Constituent Amino Acids

After degrading a whey protein hydrolysate by acid hydrolysis, the composition of constituent amino acids was measured using an amino acid autoanalyzer. Briefly, 25 mg of a whey protein hydrolysate was accurately weighed into a cap tube and then hydrolyzed at 110° C. for 24 hours after adding 2.5 mL of 6 N HCl. After removing unhydrolyzed material using a 3G-4 glass filter, the solvent was completely evaporated from the filtrate at 50° C. using a rotary vacuum evaporator (N-1110, EYELA, Tokyo, Japan). Then, 25 mL of a sample for amino acid analysis was prepared using 0.01 N HCl. Amino acid analysis was performed with an amino acid autoanalyzer (Biochrom 30, Cambridge, UK) by injecting 40 μL of the sample solution.

TABLE 2

| Amino acid (mg/g) | Example 1 | Comparative Example 3 | Comparative Example 4 | Comparative Example 5 |
| --- | --- | --- | --- | --- |
| Asp | 81.56 | 82.22 | 84.31 | 83.11 |
| Thr | 54.29 | 56.87 | 55.79 | 58.46 |
| Ser | 39.78 | 42.94 | 41.63 | 43.27 |
| Glu | 129.96 | 137.17 | 132.99 | 132.43 |
| Pro | 43.75 | 46.84 | 43.95 | 45.79 |
| Gly | 14.57 | 14.00 | 14.44 | 13.92 |
| Ala | 38.81 | 43.09 | 39.87 | 39.33 |
| Cys | 10.08 | 11.8 | 12.35 | 17.00 |
| Val | 36.91 | 39.6 | 38.98 | 37.12 |
| Met | 15.08 | 14.3 | 15.46 | 14.15 |
| Ile | 40.57 | 41.97 | 44.68 | 41.08 |
| Leu | 77.84 | 83.21 | 80.72 | 76.32 |
| Tyr | 19.55 | 22.53 | 22.34 | 19.56 |
| Phe | 24.91 | 25.6 | 25.64 | 23.66 |
| His | 13.75 | 14.41 | 14.29 | 13.48 |
| Lys | 68.32 | 72.76 | 72.09 | 67.06 |
| Arg | 18.29 | 19.43 | 17.76 | 16.14 |
| Trp | 10.63 | 11.27 | 11.60 | 10.41 |
| Ile + Leu + Val | 155.32 | 164.78 | 148.72 | 154.52 |

Test Example 8. Measurement of Molecular Weight

Figure 8:
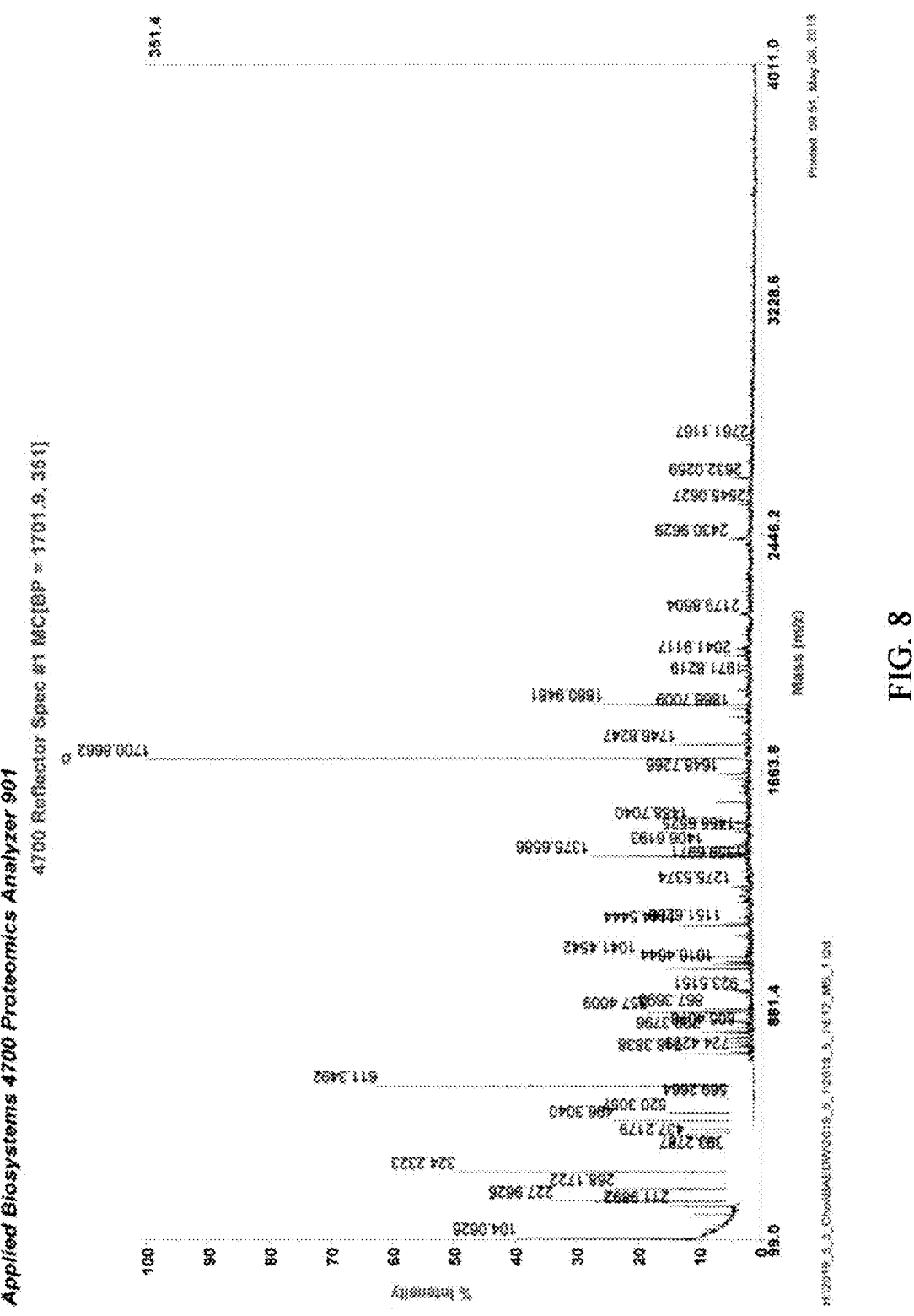
FIG. 8 shows a result of measuring the molecular weight of a hydrolysate prepared in Example 1 according to the present disclosure.
Figure 9A:
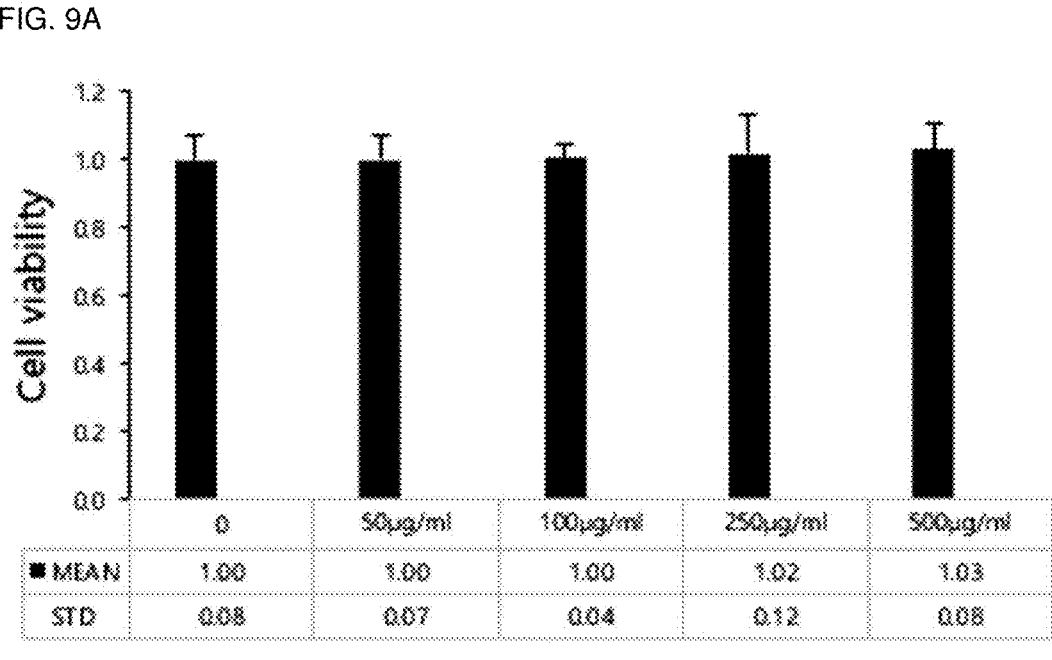
FIGS. 9*a*-9*d* show the cytotoxicity of whey protein hydrolysates of Example 1 and Comparative Examples 3-5.
Figure 9B:
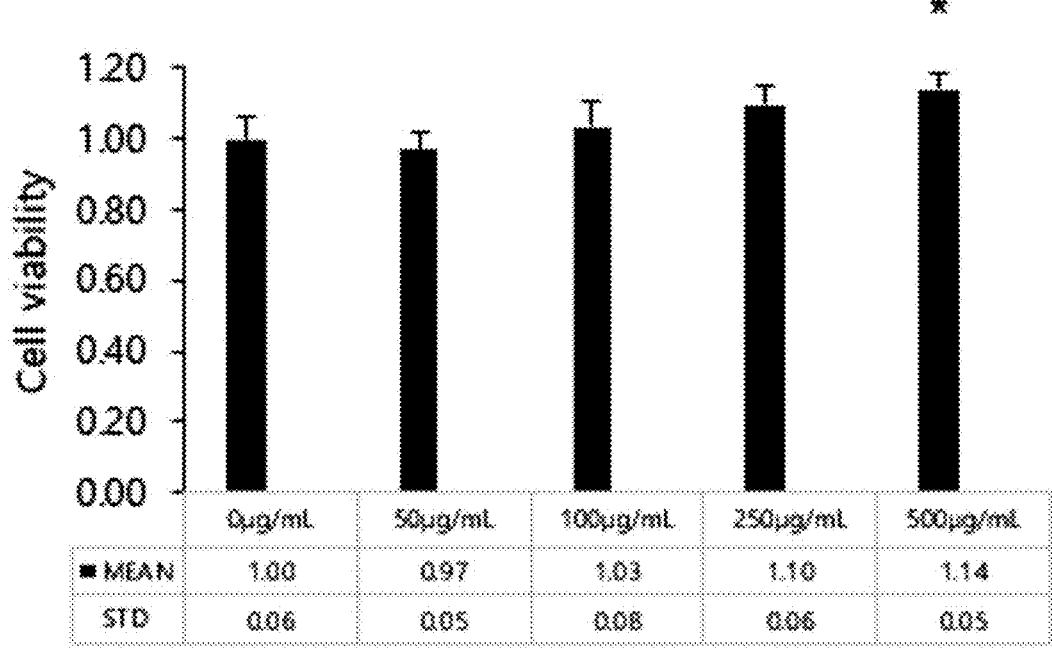
Figure 9C:
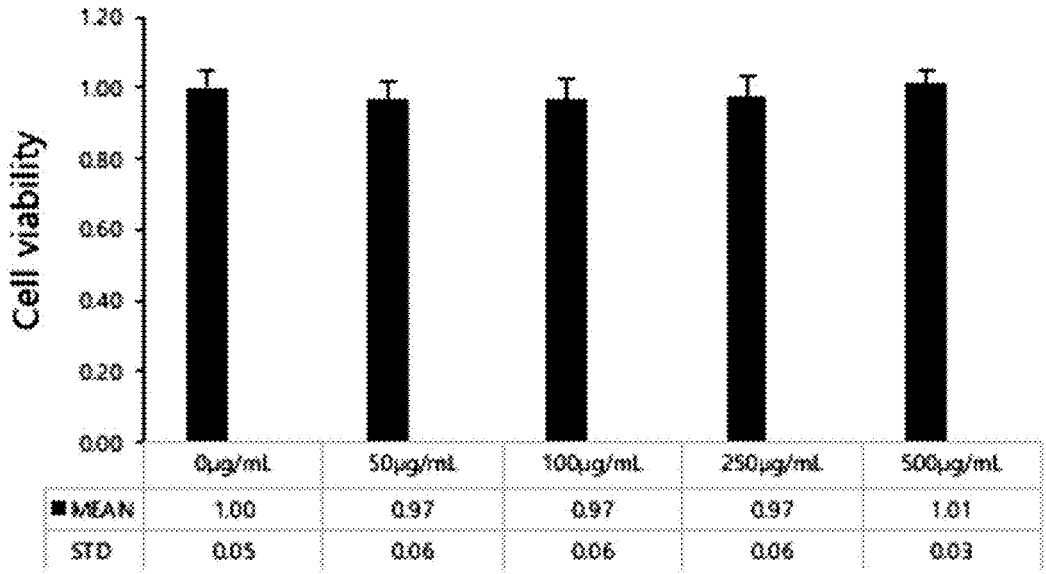
Figure 9D:
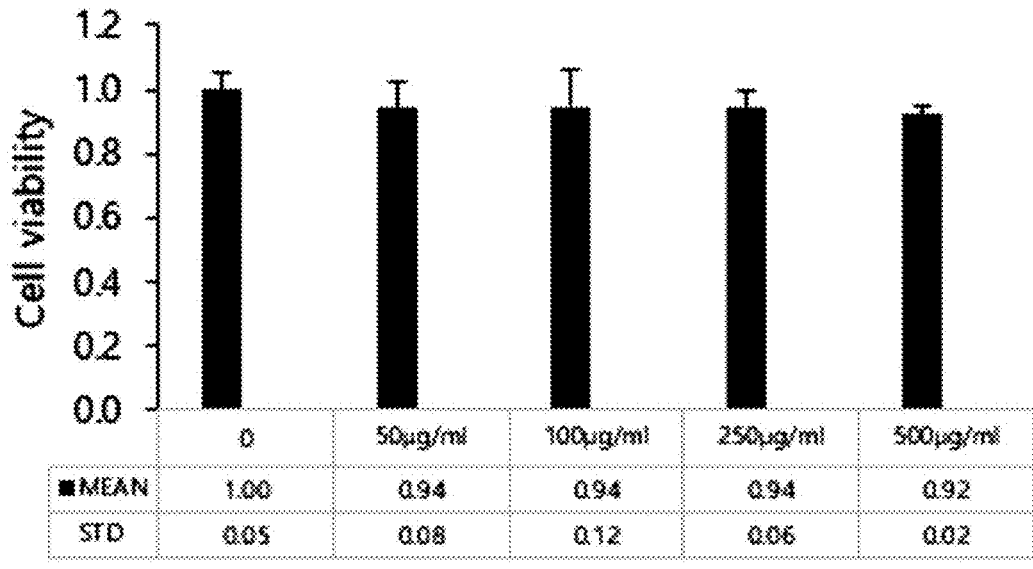

FIG. 8 shows a result of measuring the molecular weight of the hydrolysate prepared in Example 1 according to the present disclosure.

After dissolving 0.01 g of the hydrolysate of Example 1 by adding 490 μL of double distilled water and 500 μL of acetonitrile containing 0.1% TEA, mass distribution was investigated by MALDI-TOF mass spectroscopy (4700 Proteomics analyzer, Applied Biosystems, MA, USA).

As shown in FIG. 8, the molecular weight of Example 1 was 210-2800 Da. Major peptide peaks excluding the CHCA matrix peak were observed at 324 m/z, 496 m/z, 611 m/z, 1375 m/z, 1700 m/z and 1880 m/z. Many peptide peaks were observed mostly at 1700 m/z or lower.

Test Example 9. Measurement of Indicator Peptide Content

Synthesis of Indicator Peptide

An indicator peptide Leu-Asp-Ile-Gln-Lys (LDIQK) confirmed through amino acid sequencing was synthesized by AbClon (Seoul, Korea). The molecular weight and purity of the synthesized peptide LDIQK were 615.73 Da and 95.05%, respectively.

Quantification of Indicator Peptide

The indicator peptide was quantified using an Agilent 1260 infinity HPLC system (Santa Clara, CA, USA) equipped with Watchers 120 ODS-BP (4.6×250 mm, 5 μm) and a Shimadzu HPLC prominence system. The analysis condition was the same except for the analysis apparatus. 0.5 g of the sample powder of Example 1 was completely dissolved in 10 mL of HPLC-grade distilled water without any pretreatment and then centrifuged (7,500×g, 20 min). The supernatant was filtered through a 0.20-μm syringe filter and used as a sample for analysis. The concentration of soluble proteins was measured by Biuret test. The HPLC analysis condition for the quantification of the indicator peptide is described in Table 3, and the content of the indicator peptide (LDIQK) is shown in Table 4.

TABLE 3

| solvent | A, 0.1% TFA/DW:B, 0.1% TFA/acetonitrile | |
| --- | --- | --- |

| Gradient | | |
| --- | --- | --- |
| Time, min | Solvent A | Solvent B |
| 0~1 | 95 | 5 |
| 1~25 | 70 | 30 |
| 25~30 | 0 | 100 |
| 35~40 | 100 | 0 |

| Sample loading | 10 uL |
| --- | --- |
| Flow rate | 1 mL/min |
| Column temperature | 30° C. |
| Deletion | UV 220 nm |

TABLE 4

| | Example 1 | Comparative Example 3 | Comparative Example 4 | Comparative Example 5 |
| --- | --- | --- | --- | --- |
| LDIQK (mg/g) | 23.46 ± 2.47 | <0.1 ± 0.01 | 0.3 ± 0.01 | 0.6 ± 0.01 |

As shown in Table 4, the water-soluble whey protein hydrolysate prepared in Example 1 according to the present disclosure exhibited a remarkably higher indicator peptide content as compared to Comparative Examples 3-5.

Test Example 10. Measurement of Cytotoxicity

FIGS. 9a-9d show the cytotoxicity of the whey protein hydrolysates of Example 1 and Comparative Examples 3-5.

After seeding C2C12 mouse myoblasts, the cells were differentiated for 7 days after replacing the culture medium with a differentiation medium (2% horse serum) when confluence reached 90%. After the differentiation, the cells were treated with the whey protein hydrolysates of Example 1 and Comparative Examples 3-5 at different concentrations (0, 50, 100, 250 and 500 μg/mL) and cytotoxicity was measured 48 hours later.

As shown in FIGS. 9a-9d, the whey protein hydrolysates of Example 1 and Comparative Examples 3-5 showed no cytotoxicity up to 500 μg/mL.

Test Example 11. Measurement of Myotube Thickness (Diameter)

Figure 10:
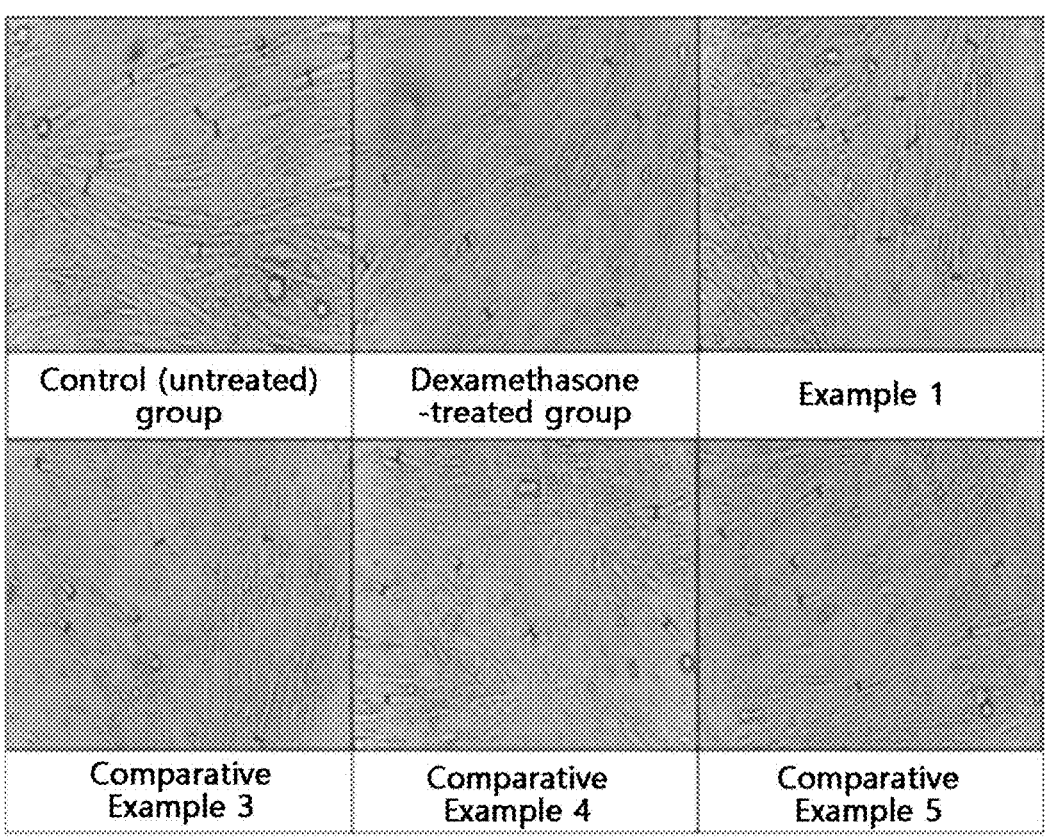
FIG. 10 shows a result of measuring the thickness of myotubes of a control (untreated) group, a dexamethasone-treated group, an Example 1 administration group and Comparative Examples 3-5 administration groups using a microscope.

FIG. 10 shows a result of measuring the thickness of myotubes of a control (untreated) group, a dexamethasone-treated group, an Example 1 administration group and Comparative Examples 3-5 administration groups using a microscope.

Figure 11:
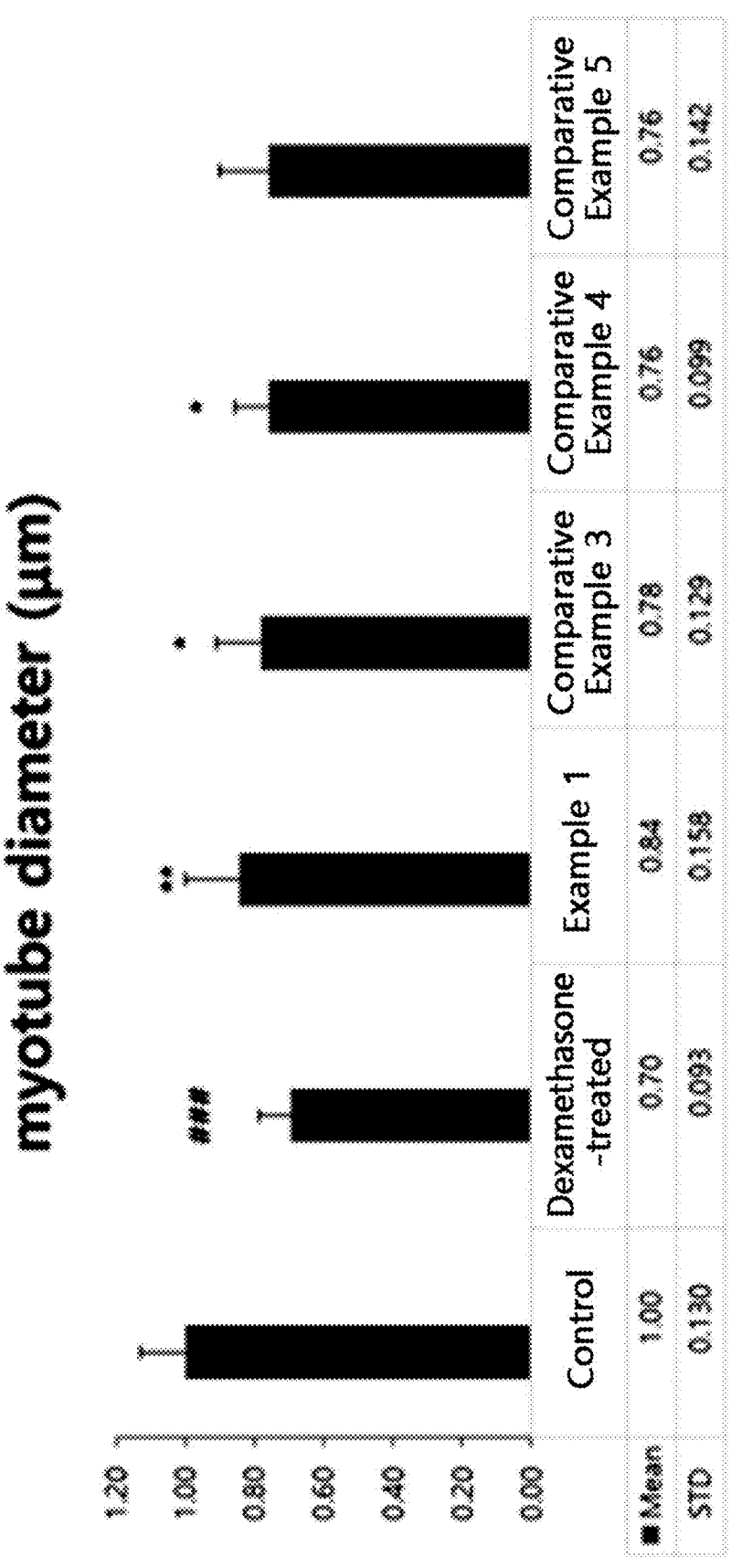
FIG. 11 shows a result of measuring the thickness of myotubes of a control (untreated) group, a dexamethasone-treated group, an Example 1 administration group and Comparative Examples 3-5 administration groups using a microscope.

FIG. 11 shows a result of measuring the thickness of myotubes of a control (untreated) group, a dexamethasone-treated group, an Example 1 administration group and Comparative Examples 3-5 administration groups using a microscope.

After seeding C2C12 mouse myoblasts, the cells were differentiated for 7 days after replacing the culture medium with a differentiation medium (2% horse serum) when confluence reached 80%. For investigation of the inhibitory effect against muscle atrophy, the cells were treated with 50 μM dexamethasone (Dexa; Sigma Aldrich, USA) and 100 μg/mL of the whey protein hydrolysate of Example 1 or Comparative Examples 3-5 for 2 days (48 hours) from day 7 after the induction of differentiation. After the culturing, the cells were imaged using an optical microscope (CKX41, Olympus) at ×400 magnification and the image was analyzed with the ImageJ software (USA). The cells were imaged at random locations and the thickness was analyzed for at least 10 myotubes (6 repetitions/group).

The C2C12 cells of a control (untreated) group were untreated, and the C2C12 cells of a dexamethasone-treated group were treated with 50 μM dexamethasone.

As shown in FIG. 10, the group treated with the water-soluble whey protein hydrolysate prepared in Example 1 according to the present disclosure showed a larger myotube thickness as compared to the dexamethasone-treated group or the groups treated with Comparative Examples 3-5.

As shown in FIG. 11, the myotube thickness was decreased by 30.4% in the dexamethasone-treated group as compared to the control (untreated) group, and the myotube thickness of the group treated with Example 1 was increased by 21% as compared to the dexamethasone-treated group (recovery rate: 48%).

In contrast, the myotube thickness of the group treated with Comparative Example 3 was increased by 12% as compared to the dexamethasone-treated group (recovery rate: 28%), and the myotube thickness of the groups treated with Comparative Example 4 and Comparative Example 5 was increased by 9% as compared to the dexamethasone-treated group (recovery rate: 21%). Accordingly, it was confirmed that the water-soluble whey protein hydrolysate of Example 1 increases the most superior effect of increasing the myotube thickness decreased by dexamethasone treatment as compared to Comparative Examples 3-5.

Figure 12:
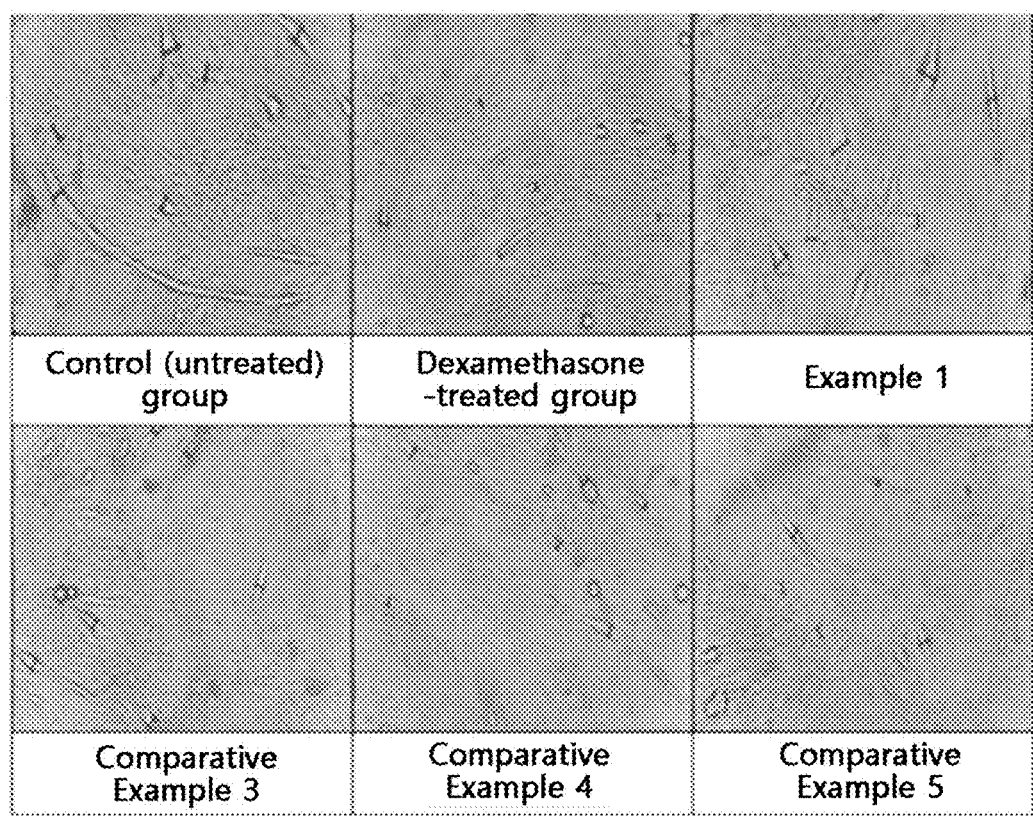
FIG. 12 shows a result of measuring the thickness of myotubes of a control (untreated) group, a dexamethasone-treated group, an Example 1 administration group and Comparative Examples 3-5 administration groups using a microscope.

Test Example 12. Measurement of Myotube Thickness (Diameter) after Correction for Protein Content FIG. 12 shows a result of measuring the thickness of myotubes of a control (untreated) group, a dexamethasone-treated group, an Example 1 administration group and Comparative Examples 3-5 administration groups using a microscope.

Figure 13:
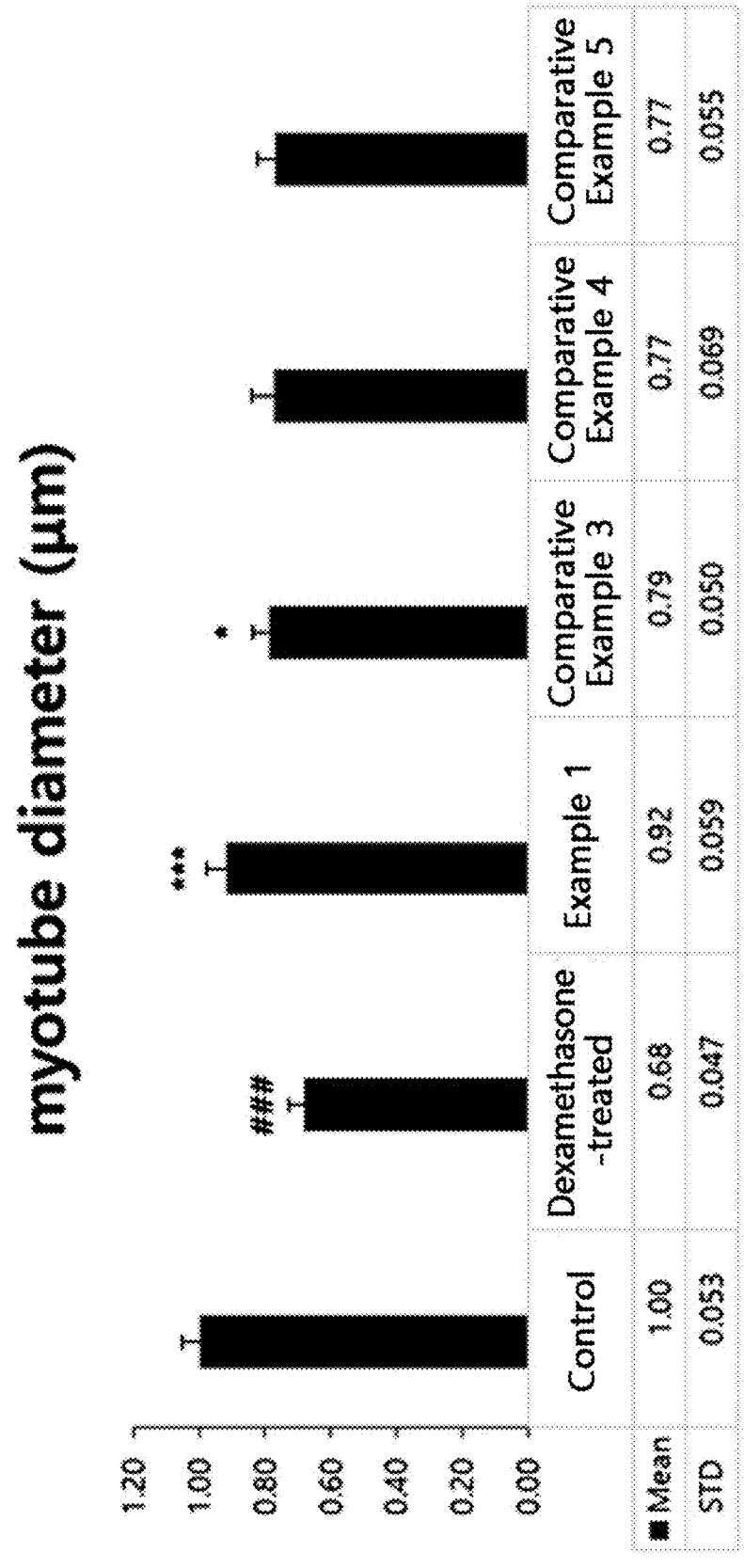
FIG. 13 shows a result of measuring the thickness of myotubes of a control (untreated) group, a dexamethasone-treated group, an Example 1 administration group and Comparative Examples 3-5 administration groups using a microscope.

FIG. 13 shows a result of measuring the thickness of myotubes of a control (untreated) group, a dexamethasone-treated group, an Example 1 administration group and Comparative Examples 3-5 administration groups using a microscope.

After seeding C2C12 mouse myoblasts, the cells were differentiated for 7 days after replacing the culture medium with a differentiation medium (2% horse serum) when confluence reached 80%. For investigation of the inhibitory effect against muscle atrophy, the cells were treated with 50 μM dexamethasone (Dexa; Sigma Aldrich, USA) and 80 μg/mL of the whey protein hydrolysate of Example 1 or Comparative Examples 3-5 for 2 days (48 hours) from day 7 after the induction of differentiation. After the culturing, the cells were imaged using an optical microscope (CKX41, Olympus) at ×400 magnification and the image was analyzed with the ImageJ software (USA). The cells were imaged at random locations and the thickness was analyzed for at least 10 myotubes (6 repetitions/group).

The C2C12 cells of a control (untreated) group were untreated, and the C2C12 cells of a dexamethasone-treated group were treated with 50 μM dexamethasone.

As shown in FIG. 12, the group treated with the water-soluble whey protein hydrolysate prepared in Example 1 according to the present disclosure showed a larger myotube thickness as compared to the dexamethasone-treated group or the groups treated with Comparative Examples 3-5.

As shown in FIG. 13, the myotube thickness was decreased by 32% in the dexamethasone-treated group as compared to the control (untreated) group, and the myotube thickness of the group treated with Example 1 was increased by 35% as compared to the dexamethasone-treated group (recovery rate: 74%).

In contrast, the myotube thickness of the group treated with Comparative Example 3 was increased by 16% as compared to the dexamethasone-treated group (recovery rate: 33%), and the myotube thickness of the groups treated with Comparative Example 4 and Comparative Example 5 was increased by 13% as compared to the dexamethasone-treated group (recovery rate: 29%). Accordingly, it was confirmed that the water-soluble whey protein hydrolysate of Example 1 increases the most superior effect of increasing the myotube thickness decreased by dexamethasone treatment as compared to Comparative Examples 3-5.

Hereinafter, formulation examples of a composition containing the whey protein hydrolysate of the present disclosure are described. However, the examples are provided only to illustrate the present disclosure and do not limit the present disclosure.

Formulation Example 1. Preparation of Powder

| | |
|---|---|
| Water-soluble whey protein hydrolysate obtained in Example 1 | 500 mg |
| Lactose | 100 mg |
| Talc | 10 mg |

A powder was prepared by mixing the above ingredients and filling in a sealed pouch.

Formulation Example 2. Preparation of Tablet

| | |
|---|---|
| Water-soluble whey protein hydrolysate obtained in Example 1 | 300 mg |
| Corn starch | 100 mg |
| Lactose | 100 mg |
| Magnesium stearate | 2 mg |

After mixing the above ingredients, a tablet was prepared according to a common tablet preparation method.

Formulation Example 3. Preparation of Capsule

| | |
|---|---|
| Water-soluble whey protein hydrolysate obtained in Example 1 | 200 mg |
| Crystalline | 3 mg |
| Lactose | 14.8 mg |
| Magnesium stearate | 0.2 mg |

After mixing the above ingredients, a capsule was prepared by filling the mixture in a gelatin capsule according to a common capsule preparation method.

Formulation Example 4. Preparation of Injection

| | |
|---|---|
| Water-soluble whey protein hydrolysate obtained in Example 1 | 600 mg |
| Mannitol | 180 mg |
| Sterilized distilled water for injection | 2974 mg |
| $Na_2HPO_4 \cdot 12H_2O$ | 26 mg |

An injection was prepared by mixing the above ingredients in an ampoule according to a common injection preparation method.

Formulation Example 5. Preparation of Liquid Formulation

| | |
|---|---|
| Water-soluble whey protein hydrolysate obtained in Example 1 | 4 g |
| High-fructose corn syrup | 10 g |
| Mannitol | 5 g |
| Purified water | Adequate |

According to a common liquid formulation preparation method, after dissolving the above ingredients in purified water and adding an adequate amount of lemon flavor, purified water was added to make the total amount 100 g. The prepared liquid formulation was filled in a brown bottle and then sterilized.

Formulation Example 6. Preparation of Granule

| | |
|---|---|
| Water-soluble whey protein hydrolysate obtained in Example 1 | 1,000 mg |
| Vitamin mixture | Adequate |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | Adequate |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

Although the above-described compositions of the vitamin and mineral mixtures are given as relatively preferred examples, they may be changed as desired. A granule may be prepared by mixing the above ingredients according to a common granule preparation method, and it may be used to prepare a functional health food composition according to a common method.

Formulation Example 7. Preparation of Functional Beverage

| | |
|---|---|
| Water-soluble whey protein hydrolysate obtained in Example 1 | 1,000 mg |
| Citric acid | 1,000 mg |
| Oligosaccharide | 100 g |
| Plum concentrate | 2 g |
| Taurine | 1 g |
| Purified water | To 900 mL |

According to a common functional beverage preparation method, after mixing the above ingredients and heating at 85° C. for about 1 under stirring, the prepared solution was filtered and filled in a sterilized 2-L container. After sealing and sterilizing, the solution was stored in a refrigerator for later use for preparation of a functional beverage composition of the present disclosure.

Although the above-described composition is given as a relatively preferred example, it may be changed as desired depending on regional and ethnic preferences such as consumers, countries, purpose of use, etc.

INDUSTRIAL APPLICABILITY

A whey protein hydrolysate of the present disclosure and a composition containing the same as an active ingredient may be used as a composition for alleviating, preventing or treating sarcopenia.

The invention claimed is:

1. A method for preparing a water-soluble whey protein hydrolysate, comprising:
   (A) a step of dissolving whey protein by mixing the whey protein with water at a weight ratio of 1:3-10;
   (B) a step of performing primary hydrolysis by adding 0.1-1 part by weight of a *Bacillus licheniformis*-derived endoprotease to 100 parts by weight of the dissolved whey protein;
   (C) a step of performing secondary hydrolysis by adding 0.1-1 part by weight of an *Aspergillus oryzae*-derived exoprotease to the primarily hydrolyzed hydrolysate; and
   (D) a step of obtaining a water-soluble whey protein hydrolysate by filtering the secondarily hydrolyzed hydrolysate to remove an insoluble substance,
   wherein the *Bacillus licheniformis*-derived endoprotease is a mixture of Alcalase and Protamex, where a weight ratio of the Alcalase and the Protamex is 1:0.5-2,
   wherein *Aspergillus oryzae*-derived exoprotease is Flavourzyme, and
   wherein a weight ratio of the mixture of Alcalase and Protamex to Flavourzyme is 2:1.

2. The method for preparing a water-soluble whey protein hydrolysate according to claim 1, which further comprises, after the step (D),
   (E) a step of sterilizing the obtained water-soluble whey protein hydrolysate and then cooling at room temperature; and
   (F) a step of drying and filtering the sterilized and cooled water-soluble whey protein hydrolysate.

3. The method for preparing a water-soluble whey protein hydrolysate according to claim 1, wherein the whey protein is derived from cheese whey.

4. The method for preparing a water-soluble whey protein hydrolysate according to claim 1, wherein the whey protein is a normal whey powder, a demineralized whey powder, a whey protein concentrate or a whey protein isolate.

5. The method for preparing a water-soluble whey protein hydrolysate according to claim 1, wherein the weight ratio of the Alcalase and the Protamex is 1:1-1.5.

6. The method for preparing a water-soluble whey protein hydrolysate according to claim 1, wherein the whey protein hydrolysate comprises the following amino acids: 9-11 mg/g of Cys, 19-22 mg/g of Tyr, 18-19 mg/g of Arg, 37-39 mg/g of Ala, 43-45 mg/g of Pro, 68-72 mg/g of Lys, 13.5-14 mg/g of His, 40-41 mg/g of Ile, 77-80 mg/g of Leu, 15-17 mg/g of Met, 24-25 mg/g of Phe, 36-37 mg/g of Val, 120-130 mg/g of Glu, 80-82 mg/g of Asp, 35-41 mg/g of Ser, 14.5-15 mg/g of Gly, 54-55 mg/g of Thr and 10-11 mg/g of Trp.

7. The method for preparing a water-soluble whey protein hydrolysate according to claim 1, wherein the whey protein hydrolysate comprises 1-5 wt % of free amino acids based on total amino acids.

8. The method for preparing a water-soluble whey protein hydrolysate according to claim 1, wherein the whey protein hydrolysate comprises 155-180 mg/g of BCAA amino acids.

9. The method for preparing a water-soluble whey protein hydrolysate according to claim 1, wherein the whey protein hydrolysate is for use in the manufacture of a medicament for improving muscle function.

10. The method for preparing a water-soluble whey protein hydrolysate according to claim 1, wherein the whey protein hydrolysate is for use in the manufacture of a medicament for treating or preventing sarcopenia.

\* \* \* \* \*

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Atrogin1 F

<400> SEQUENCE: 1
agaaagaaag acattcagaa ca                                              22

<210> SEQ ID NO 2
<211> LENGTH: 18
<212> TYPE: DNA
<213> ORGANISM: Artificial Sequence
<220> FEATURE:
<223> OTHER INFORMATION: Atrogin1 R

<400> SEQUENCE: 2
gctccttcgt acttcctt                                                  18

<210> SEQ ID NO 3
<211> LENGTH: 20
<212> TYPE: DNA
<213> ORGANISM: Artificial Sequence
<220> FEATURE:
<223> OTHER INFORMATION: MurF1 F

<400> SEQUENCE: 3
aagactgagc tgagtaactg                                                20

<210> SEQ ID NO 4
<211> LENGTH: 20
<212> TYPE: DNA
<213> ORGANISM: Artificial Sequence
<220> FEATURE:
<223> OTHER INFORMATION: MurF1 R

<400> SEQUENCE: 4
tagagggtgt caaacttctg                                                20

<210> SEQ ID NO 5
<211> LENGTH: 22
<212> TYPE: DNA
<213> ORGANISM: Artificial Sequence
<220> FEATURE:
<223> OTHER INFORMATION: Bnip3 F

<400> SEQUENCE: 5
```

-continued

```
ttccactagc accttctgat ga                                                        22

<210> SEQ ID NO 6
<211> LENGTH: 22
<212> TYPE: DNA
<213> ORGANISM: Artificial Sequence
<220> FEATURE:
<223> OTHER INFORMATION: Bnip3 R

<400> SEQUENCE: 6
gaacaccgca tttacagaac aa                                                         22

<210> SEQ ID NO 7
<211> LENGTH: 18
<212> TYPE: DNA
<213> ORGANISM: Artificial Sequence
<220> FEATURE:
<223> OTHER INFORMATION: Gapdh F

<400> SEQUENCE: 7
tcggtgtgaa cggatttg                                                             18

<210> SEQ ID NO 8
<211> LENGTH: 18
<212> TYPE: DNA
<213> ORGANISM: Artificial Sequence
<220> FEATURE:
<223> OTHER INFORMATION: Gapdh R

<400> SEQUENCE: 8
ggtctcgctc ctggaaga                                                             18
```